US012582338B2

(12) United States Patent
Boud et al.

(10) Patent No.: US 12,582,338 B2
(45) Date of Patent: Mar. 24, 2026

(54) BLOOD DRAW DEVICE HAVING TACTILE FEEDBACK MECHANISM

(71) Applicant: Becton, Dickinson and Company, Franklin Lakes, NJ (US)

(72) Inventors: Adam J. Boud, Bluffdale, UT (US); Curtis H. Blanchard, Herriman, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 670 days.

(21) Appl. No.: 17/972,735

(22) Filed: Oct. 25, 2022

(65) Prior Publication Data

US 2023/0136086 A1 May 4, 2023

Related U.S. Application Data

(60) Provisional application No. 63/273,226, filed on Oct. 29, 2021.

(51) Int. Cl.
 A61B 5/00 (2006.01)
 A61B 5/15 (2006.01)
 A61M 25/01 (2006.01)

(52) U.S. Cl.
 CPC .. A61B 5/150816 (2013.01); A61B 5/150992 (2013.01); *A61M 25/0113* (2013.01)

(58) Field of Classification Search
 CPC ........ A61B 5/150816; A61B 5/150992; A61B 5/150656; A61B 5/150717; A61B 5/150809; A61B 5/150259; A61B 5/15003; A61B 5/153; A61B 5/150206; A61M 25/0113; A61M 2205/581; A61M 2205/582; A61M 25/0693
See application file for complete search history.

(56) References Cited

U.S. PATENT DOCUMENTS

| | | | |
|---|---|---|---|
| 6,346,074 B1 | 2/2002 | Roth | |
| 8,062,226 B2 * | 11/2011 | Moore | A61B 8/4461 |
| | | | 600/467 |
| 8,267,911 B2 * | 9/2012 | Gallogly | A61B 5/153 |
| | | | 604/408 |
| 8,690,833 B2 * | 4/2014 | Belson | A61M 5/158 |
| | | | 604/510 |

(Continued)

*Primary Examiner* — May A Abouelela
(74) *Attorney, Agent, or Firm* — The Webb Law Firm

(57) ABSTRACT

A blood draw device including an introducer and an actuator. The introducer has a proximal end portion, a distal end portion, and an inner volume, and includes a top surface having a first portion of a first length and a second portion of a second length. The first portion may have a smooth surface along the first length and the second portion has a plurality of ridges along the second length. The actuator includes an exterior portion positioned above the top surface and an interior portion positioned within the inner volume, wherein the exterior portion of the actuator includes an engagement member and a downwardly-extending tab projecting below the engagement member such that the downwardly-extending tab of the actuator may contact at least the plurality of ridges of the second portion of the introducer to provide at least one of tactile and audible feedback to a user.

9 Claims, 15 Drawing Sheets

(56) References Cited

U.S. PATENT DOCUMENTS

| | | | |
|---|---|---|---|
| 8,728,038 B2 * | 5/2014 | Spearman ........ | A61B 5/150244 |
| | | | 600/468 |
| 8,728,058 B2 * | 5/2014 | Schertiger ......... | A61M 25/0074 |
| | | | 604/544 |
| 9,186,100 B2 * | 11/2015 | Devgon ........... | A61B 5/150717 |
| 9,744,344 B1 * | 8/2017 | Devgon ........... | A61M 39/0247 |
| 11,406,795 B2 * | 8/2022 | Burkholz .......... | A61B 5/15003 |
| 11,918,357 B2 * | 3/2024 | Devgon ........... | A61B 5/150732 |
| 2003/0120222 A1 | 6/2003 | Vaillancourt | |
| 2014/0100529 A1 * | 4/2014 | Ito .................... | A61M 25/0631 |
| | | | 604/164.08 |
| 2014/0364766 A1 * | 12/2014 | Devgon ........... | A61B 5/150396 |
| | | | 600/581 |
| 2015/0314104 A1 | 11/2015 | Almansouri et al. | |
| 2015/0360005 A1 * | 12/2015 | Arellano Cabrera ........................ | |
| | | | A61M 25/0631 |
| | | | 604/110 |
| 2016/0166772 A1 * | 6/2016 | Mirzazadeh ...... | A61M 5/31513 |
| | | | 604/222 |
| 2017/0216564 A1 | 8/2017 | Devgon et al. | |
| 2018/0272107 A1 * | 9/2018 | Ehrenreich ...... | A61B 5/150748 |
| 2019/0275302 A1 * | 9/2019 | Devgon ........... | A61B 5/150259 |
| 2021/0290264 A1 | 9/2021 | Harding et al. | |
| 2022/0305236 A1 | 9/2022 | Harding et al. | |
| 2022/0313958 A1 | 10/2022 | Harding et al. | |

* cited by examiner

BLOOD DRAW DEVICE HAVING TACTILE FEEDBACK MECHANISM

CROSS-REFERENCE TO RELATED APPLICATION

The present application claims priority to U.S. Provisional Application Ser. No. 63/273,226, entitled "Blood Draw Device Having Tactile Feedback Mechanism", filed Oct. 29, 2021, the entire disclosure of which is hereby incorporated by reference in its entirety.

BACKGROUND OF THE INVENTION

Field of the Invention

The embodiments described herein relate generally to fluid transfer medical devices. More particularly, the embodiments described herein relate to blood draw device for withdrawing blood from from a patient through a placed peripheral intravenous catheter, with the blood draw device having one or more tactile feedback mechanisms.

Description of Related Art

A catheter is commonly used to infuse fluids into vasculature of a patient. For example, the catheter may be used for infusing normal saline solution, various medicaments, or total parenteral nutrition. Furthermore, the catheter may also be used for withdrawing blood from the patient.

The catheter may be an over-the-needle peripheral intravenous catheter (PIVC). In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient. After proper placement of the needle, the clinician may temporarily occlude flow in the vasculature and remove the needle, leaving the catheter in place (i.e., "indwelled") for future blood withdrawal and/or fluid infusion.

While PIVCs may be used for blood withdrawal, they are not typically designed and optimized for such purposes. Accordingly, several blood draw devices have been developed for use with PIVCs to improve blood collection. These devices (such as, e.g. PIVO™ from Velano Vascular, Inc.) are configured as single-use devices which temporarily attach to a PIVC to draw a blood sample. Using an existing peripheral intravenous line as a conduit to the vasculature, the blood draw device includes an introducer and an actuator configured to enable a user to manually advance a flexible, internal flow tube through the PIVC, beyond the catheter tip, and into the vein to collect a blood sample. This flow tube is designed to extend beyond any suboptimal draw conditions around the indwelling line to reach vein locations where blood flow is optimal for aspiration. Once blood collection is complete, the flow tube is retracted, and the device is removed from the PIVC and discarded.

In some instances, blood draw devices for use with PIVCs include features to provide tactile feedback to the user indicative of the position of the flow tube relative to the indwelled catheter. Examples of such devices are shown and described in U.S. patent application Ser. No. 16/419,191, which is incorporated herein by reference in its entirety. For example, in the embodiments described in U.S. patent application Ser. No. 16/419,191, the introducer of the blood draw device includes a plurality of ribs or ridges extending across a top surface thereof, with two unique regions of ridges being provided. As the user slides the actuator along the introducer, the transition between these two regions is intended to provide tactile feedback to the user indicative of the position of the flow tube as it enters the patient's vein. However, due to the ridges being formed across a substantial portion of the introducer, movement of the actuator along the introducer may result in vibrations felt by the user, with these vibrations interfering with the user's ability to distinguish tactile feedback from the flow tube should the flow tube encounter any obstructions, obstacles, or resistance encountered through contact with valves or other vein anatomy. Furthermore, these vibrations may be extreme enough to limit the user's ability to distinguish the location at which the ridges change shape and/or frequency, thereby reducing the intended functionality of the ridges.

SUMMARY OF THE INVENTION

Accordingly, the present disclosure generally relates to assemblies, systems, and methods including blood draw devices having introducers and/or actuators configured for improved tactile feedback.

In accordance with an aspect of the present disclosure, a blood draw device for use with a peripheral intravenous catheter (PIVC) is provided. The blood draw device may include an introducer having a proximal end portion, a distal end portion, and an inner volume, the introducer further including a top surface having a first portion of a first length and a second portion of a second length, wherein the first portion has a smooth surface along the first length and the second portion has a plurality of ridges along the second length. The blood draw device may also include an actuator having an exterior portion positioned above the top surface of the introducer and an interior portion positioned within the inner volume of the introducer, wherein the exterior portion of the actuator includes an engagement member and a downwardly-extending tab projecting below the engagement member, the actuator configured to move relative to the introducer such that the downwardly-extending tab of the actuator contacts at least the plurality of ridges of the second portion of the introducer to provide at least one of tactile and audible feedback to a user as the actuator reaches the second portion of the introducer.

In some embodiments, the second portion of the top surface of the introducer is positioned proximate the distal end portion of the introducer.

In some embodiments, the second length of the second portion on the top surface is shorter than the first length of the first portion on the top surface.

In some embodiments, the top surface of the introducer further may include a convex protrusion located proximate to the proximal end portion of the introducer, and a concave indentation located proximally and adjacent to the convex protrusion.

In some embodiments, the downwardly-extending tab of the actuator is configured to engage with the concave indentation of the introducer when the actuator is positioned at a proximate-most position relative to the introducer to prevent movement of the actuator without distally-directed force on the engagement member of the actuator.

In some embodiments, a transition from the first portion to the second portion of the introducer is configured to correspond with a distal position of a flow tube coupled to the actuator extending beyond a distal tip of an indwelling catheter within a patient.

In some embodiments, the introducer further includes a slot extending thereon, and a portion of the actuator may extend through the slot to couple the exterior portion of the actuator with the interior portion of the actuator.

In accordance with another aspect of the present disclosure, a blood draw device for use with a peripheral intravenous catheter (PIVC) is provided. The blood draw device may include an introducer having a proximal end portion, a distal end portion, and an inner volume, the introducer further including a top surface having a first convex protrusion located proximate the proximal end portion, a second convex protrusion located proximate the distal end portion, and a smooth surface extending between the first convex protrusion and the second convex protrusion. The blood draw device may further include an actuator having an exterior portion positioned above the top surface of the introducer and an interior portion positioned within the inner volume of the introducer, wherein the exterior portion of the actuator includes an engagement member and a downwardly-extending tab projecting below the engagement member, the actuator configured to move relative to the introducer such that the downwardly-extending tab of the actuator contacts at least the first convex protrusion and the second convex protrusion to provide at least one of tactile and audible feedback to a user as the actuator reaches travels over the first convex protrusion and the second convex protrusion.

In some embodiments, the blood draw device may further include a first concave indentation positioned proximally to the first convex protrusion and a second concave indentation positioned proximally to the second convex protrusion.

In some embodiments, the downwardly-extending tab of the actuator is configured to engage with the first concave indentation of the introducer when the actuator is positioned at a proximate-most position relative to the introducer, and the downwardly-extending tab of the actuator is configured to engage with the second concave indentation of the introducer when the actuator is positioned at a distal-most position relative to the introducer.

In some embodiments, the introducer further includes a slot extending thereon, and a portion of the actuator may extend through the slot to couple the exterior portion of the actuator with the interior portion of the actuator.

In accordance with another aspect of the present disclosure, a blood draw device for use with a peripheral intravenous catheter (PIVC) is provided. The blood draw device may include an introducer having a proximal end portion, a distal end portion, and an inner volume, the introducer further including an exterior top surface and an interior upper surface, the interior upper surface having at least a first portion of a first length and a second portion of a second length, wherein at least one of the first portion and the second portion of the interior upper surface includes a plurality of ridges formed thereon. The blood draw device may also include an actuator having an exterior portion positioned above a top surface of the introducer and an interior portion positioned within the inner volume of the introducer, wherein the exterior portion of the actuator includes an engagement member and the interior portion includes an upwardly-extending tab projecting towards the interior upper surface of the introducer, the actuator configured to move relative to the introducer such that the upwardly-extending tab of the introducer contacts the plurality of ridges formed on at least one of the first portion and the second portion of the interior upper surface of the introducer.

In some embodiments, both the first portion and the second portion of the interior upper surface include a plurality of ridges formed thereon.

In some embodiments, the plurality of ridges formed on the second portion are larger than the plurality of ridges formed on the second portion.

In some embodiments, the first portion of the interior upper surface is a smooth surface and the second portion of the interior upper surface includes a plurality of ridges formed thereon.

In some embodiments, the second length of the second portion on the interior upper surface is shorter than the first length of the first portion on the interior upper surface In some embodiments, the interior upper surface of the introducer further includes a convex protrusion located proximate to the proximal end portion of the introducer, and a concave indentation located proximally and adjacent to the convex protrusion.

In some embodiments, the upwardly-extending tab of the actuator is configured to engage with the concave indentation of the introducer when the actuator is positioned at a proximate-most position relative to the introducer to prevent movement of the actuator without distally-directed force on the engagement member of the actuator.

In some embodiments, the upwardly-extending tab of the actuator is positioned on a cantilever.

In some embodiments, the actuator may further includes a spring member configured to provide for releasable engagement of the actuator with a detent formed on the interior upper surface of the introducer.

Further details and advantages of the invention will become clear upon reading the following detailed description in conjunction with the accompanying drawing figures, wherein like parts are designated with like reference numerals throughout.

DETAILED DESCRIPTION

Figures 1, 2:
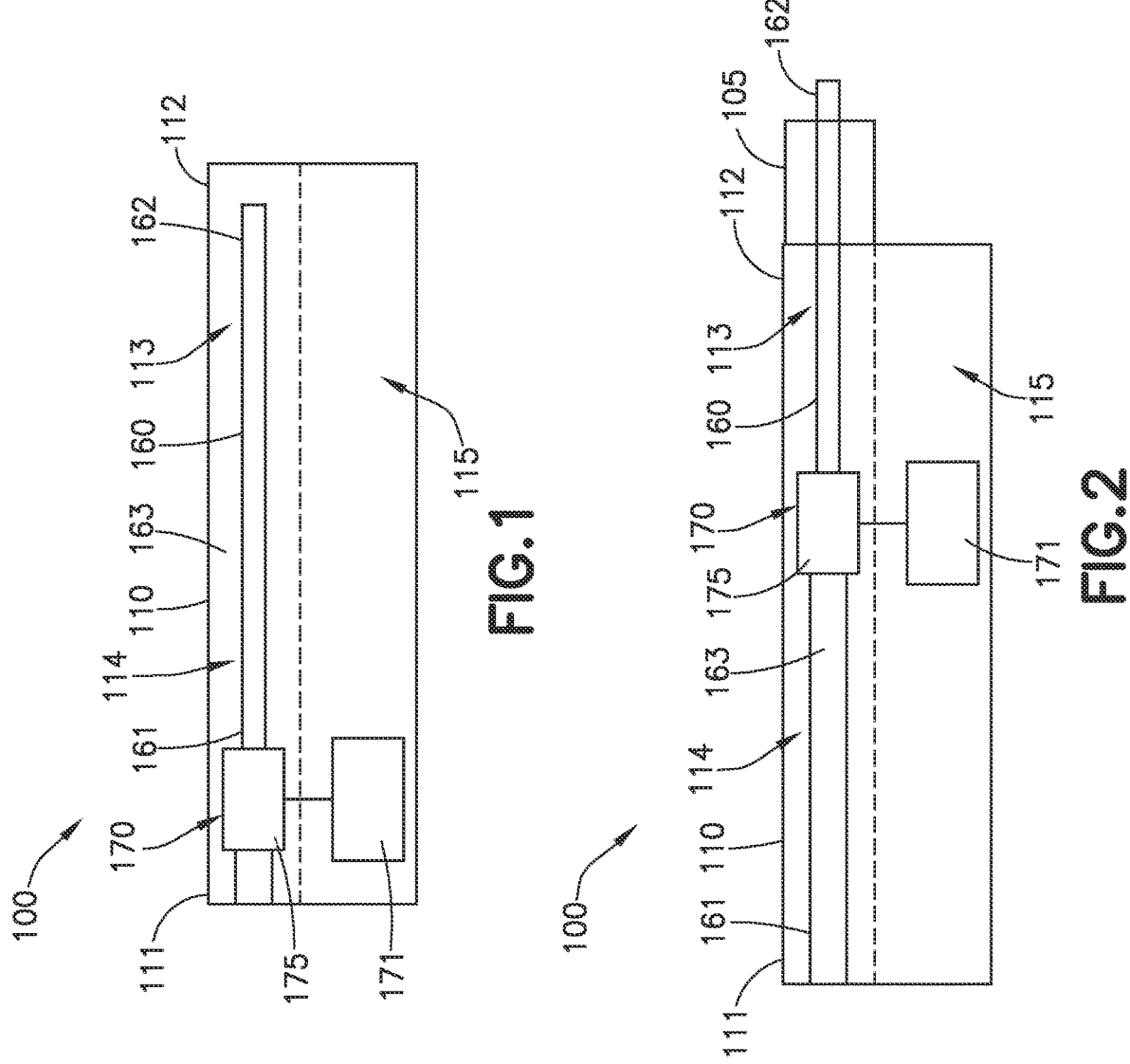
FIG. 1 is a schematic illustration of a blood draw device in a first configuration in accordance with an aspect of the present disclosure.
FIG. 2 is a schematic illustration of the blood draw device of FIG. 1 in a second configuration in accordance with an aspect of the present disclosure.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present disclosure.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Embodiments of the present disclosure will primarily be described in the context of blood draw devices for use with integrated PIVCs. However, embodiments of the present disclosure equally extend to any fluid transfer device. Accordingly, the techniques and features of the present disclosure can be applied to any type of fluid transfer device, and is not limited to blood draw via an integrated PIVC.

FIGS. 1 and 2 are schematic illustrations of a blood draw device 100 for phlebotomy through a peripheral intravenous line or catheter in a first configuration and second configuration, respectively, according to an aspect of the present disclosure. The blood draw device 100 can be any suitable shape, size, and/or configuration. As described in further detail herein, the blood draw device 100 is configured to couple to and/or otherwise engage an indwelling peripheral intravenous catheter (PIVC) 105 to transfer fluid from (e.g., aspiration of blood) and/or transfer fluid to (e.g., infusion of a drug or substance) a portion of a patient.

The blood draw device 100 includes at least an introducer 110, a catheter 160 (or cannula), and an actuator 170. The introducer 110 can be any suitable configuration. For example, in some embodiments, the introducer 110 can be an elongate member having a substantially circular or U-shaped cross-sectional shape. In some embodiments, the shape of the introducer 110 and/or one or more features or surface finishes of at least an outer surface of the introducer 110 can be arranged to increase the ergonomics of the blood draw device 100, which in some instances, can allow a user to manipulate the blood draw device 100 with one hand (i.e., single-handed use).

The introducer 110 has a proximal end portion 111 and a distal end portion 112 and defines an inner volume 113. Although not shown in FIGS. 1 and 2, the proximal end portion 111 of the introducer 110 can include an opening or port configured to movably receive a portion of the catheter 160. As such, a first portion of the catheter 160 can be disposed within the inner volume 113 and a second portion of the catheter 160 can be disposed outside of the inner volume 113. The opening or port can be any suitable configuration. For example, in some embodiments, the opening and/or port can include a seal or the like configured to form a substantially fluid tight seal with an outer surface of the portion of the catheter 160 disposed therein. In other embodiments, the arrangement of the opening and/or port can be such that a user can place the catheter 160 in selective contact with a surface of the proximal end portion 111 defining the opening and/or port, which in turn, can clamp and/or pinch the catheter 160 to selectively obstruct a lumen of the catheter 160.

The distal end portion 112 of the introducer 110 includes and/or is coupled to a lock configured to physically and fluidly couple the introducer 110 to the PIVC 105 (see e.g., FIG. 2). For example, in some embodiments, the distal end portion 112 can include a coupler or the like such as a Luer Lok™ or the like configured to physically and fluidly couple to an associated coupler of the lock. In some embodiments, the lock is configured to selectively engage and/or contact the PIVC 105 to couple the introducer 110 thereto. For example, in some embodiments, the shape, size, and/or arrangement of the lock is such that the lock forms three points of contact with the PIVC 105. In some embodiments, such an arrangement can provide structural rigidity and/or support to the PIVC 105 as a portion of the lock (e.g., a blunt cannula or the like) is inserted into a portion of the PIVC 105.

In some embodiments, the distal end portion 112 of the introducer 110 (and/or the lock) can include a seal or the like that can be transferred from a sealed configuration to a substantially open configuration to place at least a portion of the inner volume 113 in fluid communication with the lock. In some embodiments, the seal can include back flow prevention mechanism such as a one-way valve or the like that can allow, for example, the catheter 160 to be advanced in the distal direction therethrough while limiting and/or substantially preventing a fluid flow, outside the catheter 160, in the proximal direction through the seal.

As described above, the introducer 110 defines the inner volume 113, which extends between the proximal end portion 111 and the distal end portion 112. The inner volume 113 has and/or defines a first portion 114 configured to receive a first portion 171 of the actuator 170 and a second portion 115 configured to receive the catheter 160 and a second portion 175 of the actuator 170, as shown in FIGS. 1 and 2. More specifically, an inner surface of the introducer 110 that defines the inner volume 113 can have, for example, a tortuous cross-sectional shape (not shown in FIGS. 1 and 2) such that an axis defined by the first portion 114 of the inner volume 113 is parallel to and offset from an axis defined by the second portion 115 of the inner volume 113. In this manner, the first portion 114 of the inner volume 113 can be spaced apart from the second portion 115 of the inner volume 113 without being fluidically isolated therefrom. In some embodiments, the first portion 114 of the inner volume 113 can extend through a wall of the introducer 110. In other words, the introducer 110 can define a slot, channel, track, opening, and/or the like that is in fluid communication with the first portion 114 of the inner volume 113. Conversely, the second portion 115 of the inner volume 113 can be entirely defined and/or enclosed (at least in the circumferential direction) by the introducer 110. Moreover, in some embodiments, the tortuous cross-sectional shape of the inner volume 113 is such that the second portion 115 cannot be viewed (e.g., is out of the line of sight) via the slot or the like in fluid communication with the first portion 114 of the inner volume 113, which in turn, can limit and/or substantially prevent contamination of the catheter 160 disposed therein.

The catheter 160 of the blood draw device 100 includes a proximal end portion 161 and a distal end portion 162 and defines a lumen 163 that extends through the proximal end portion 161 and the distal end portion 162. The catheter 160 is movably disposed within the second portion 115 of the inner volume 113 defined by the introducer 110 and is coupled to the actuator 170. In some embodiments, the catheter 160 can be moved (e.g., via movement of the actuator 170) between a first position and a second position to transition the transfer device 100 between the first configuration and the second configuration, respectively. More specifically, at least the distal end portion 162 of the catheter 160 is disposed within the second portion 115 of the inner volume 113 when the catheter 160 is in the first position (FIG. 1) and at least a portion of the catheter 160 extends through the PIVC 105 to place a distal end of the catheter 160 in a distal position relative to a portion of the PIVC 105 when the catheter 160 is in the second position (FIG. 2). Although not shown in FIGS. 1 and 2, in some embodiments, the blood draw device 100 can include a secondary catheter or the like that is coupled to the actuator 170 and in fluid communication with the catheter 160. In such embodiments, the secondary catheter can be, for example, disposed in a proximal position relative to the catheter 160 and can be configured to extend through the opening and/or port defined by the proximal end portion 111 of the introducer 110. In this manner, a proximal end portion of the secondary catheter can be coupled to a fluid reservoir, fluid source, syringe, and/or the like, which in turn, places the catheter 160 in fluid communication therewith. Moreover, in embodiments including the secondary catheter, the catheter 160 can be entirely disposed within the introducer 110 when the catheter 160 is in the first position.

The catheter 160 can be any suitable shape, size, and/or configuration. For example, in some embodiments, at least a portion of the catheter 160 can have an outer diameter (e.g., between a 16-gauge and a 26-gauge) that is substantially similar to or slightly smaller than an inner diameter defined by a portion of the lock coupled to the distal end portion 112 of the introducer 110. In this manner, an inner surface of the portion of the lock can guide the catheter 160 as the catheter 160 is moved between the first position and the second position. In some embodiments, such an arrangement can limit and/or can substantially prevent bending, deforming, and/or kinking of the catheter 160 as the catheter 160 is moved between the first position and the second position. In some embodiments, the catheter 160 can have a length that is sufficient to place a distal surface of the catheter 160 in a desired position relative to a distal surface of the PIVC 105 when the catheter 160 is in the second position. In other words, the length of the catheter 160 can be sufficient to define a predetermined and/or desired distance between the distal surface of the catheter 160 and the distal surface of the PIVC 105 when the catheter 160 is in the second position. In some instances, placing the distal surface of the catheter 160 the predetermined and/or desired distance from the distal surface of the PIVC 105 can, for example, place the distal surface of the catheter 160 in a desired position within a patient's vein.

The catheter 160 can be formed from any suitable material or combination of materials, which in turn, can result in the catheter 160 having any suitable stiffness or durometer. In some embodiments, at least a portion of the catheter 160 can be formed of a braided material or the like, which can change, modify, and/or alter a flexibility of the catheter 160 in response to a bending force or the like. In some embodiments, forming the catheter 160 of the braided material or the like can reduce a likelihood of kinking and/or otherwise deforming in an undesired manner. In addition, forming at least a portion of the catheter 160 of a braided material can result in a compression and/or deformation in response to a compression force exerted in a direction of a longitudinal centerline defined by the catheter 160 (e.g., an axial force or the like). In this manner, the catheter 160 can absorb a portion of force associated with, for example, impacting an obstruction or the like.

The actuator 170 of the transfer device 100 can be any suitable shape, size, and/or configuration. As described above, the actuator 170 includes the first portion 171 movably disposed within the first portion 114 of the inner volume 113 and the second portion 175 movably disposed within the second portion 115 of the inner volume 113 and coupled to the catheter 160. Although not shown in FIGS. 1 and 2, the actuator 170 can have a cross-sectional shape that is associated with and/or otherwise corresponds to the cross-sectional shape of the inner volume 113 (e.g., the tortuous cross-sectional shape). Thus, an axis defined by the first portion 171 of the actuator 170 is parallel to and offset from an axis defined by the second portion 175 of the actuator 170.

The arrangement of the actuator 170 and the introducer 110 is such that the first portion 171 extends through the slot or the like in fluid communication with the first portion 114 of the inner volume 113. As such, a first region of the first portion 171 of the actuator 170 is disposed outside of the introducer 110 and a second region of the first portion 171 of the actuator 170 is disposed in the first portion 114 of the inner volume 113. In this manner, a user can engage the first region of the first portion 171 of the actuator 170 and can move the actuator 170 longitudinally relative to the introducer 110 to move the catheter 160 coupled to the second portion 175 of the actuator 170 between the first position and the second position. Although not shown in FIGS. 1 and 2, in some embodiments, the first portion 171 of the actuator 170 can include a tab, protrusion, and/or surface that is in contact with an outer surface of the introducer 110. In such embodiments, and as will be described in further detail below, the outer surface of the introducer 110 can include, for example, a set of ribs, ridges, bumps, grooves, and/or the like along which the tab, protrusion, and/or surface of the first portion 171 advances when the actuator 170 is moved relative to the introducer 110, which in turn, produces tactile feedback to provide an indication to the user associated with a position of the distal end portion 162 of the catheter 160.

In some embodiments, the blood draw device 100 can be disposed in the first configuration prior to use (e.g., shipped, stored, prepared, etc. in the first configuration). In use, a user can manipulate the blood draw device 100 to couple the introducer 110 to the indwelling PIVC 105 (e.g., via the lock coupled to and/or assembled with the introducer 110). With the blood draw device 100 coupled to the PIVC 105, the user can engage the first portion 171 of the actuator 170 to move the actuator 170 relative to the introducer 110, which in turn, moves the catheter 160 from the first position (e.g., disposed within the introducer 110) toward the second position. In some embodiments, the arrangement of the actuator 170 and the introducer 110 is such that advancing the actuator 170 relative to the introducer 110 produces a tactile output and/or feedback configured to provide and indicator associated with position of the distal end portion 162 of the catheter 160 relative to the introducer 110 and/or the PIVC 105 to the user.

With the catheter 160 in the second position (e.g., with the blood draw device 100 in the second configuration shown in FIG. 2), the user can establish fluid communication between a fluid reservoir, fluid source, syringe, and/or the like and the catheter 160. For example, as described above, in some embodiments, the user can couple the secondary catheter (not shown) to the fluid reservoir, fluid source, syringe, and/or the like. Although described as establishing fluid communication between the catheter 160 and the fluid reservoir or fluid source after placing the catheter 160 in the second position, in other embodiments, the user can establish fluid communication between the catheter 160 and the fluid reservoir or fluid source prior to moving the actuator 170 relative to the introducer 110. With the catheter 160 in fluid communication with the fluid reservoir and/or fluid source, the transfer device 100 can then transfer a fluid from the patient or transfer a fluid to the patient via the catheter 160 extending through and beyond the PIVC 105.

Figures 3A, 3B:
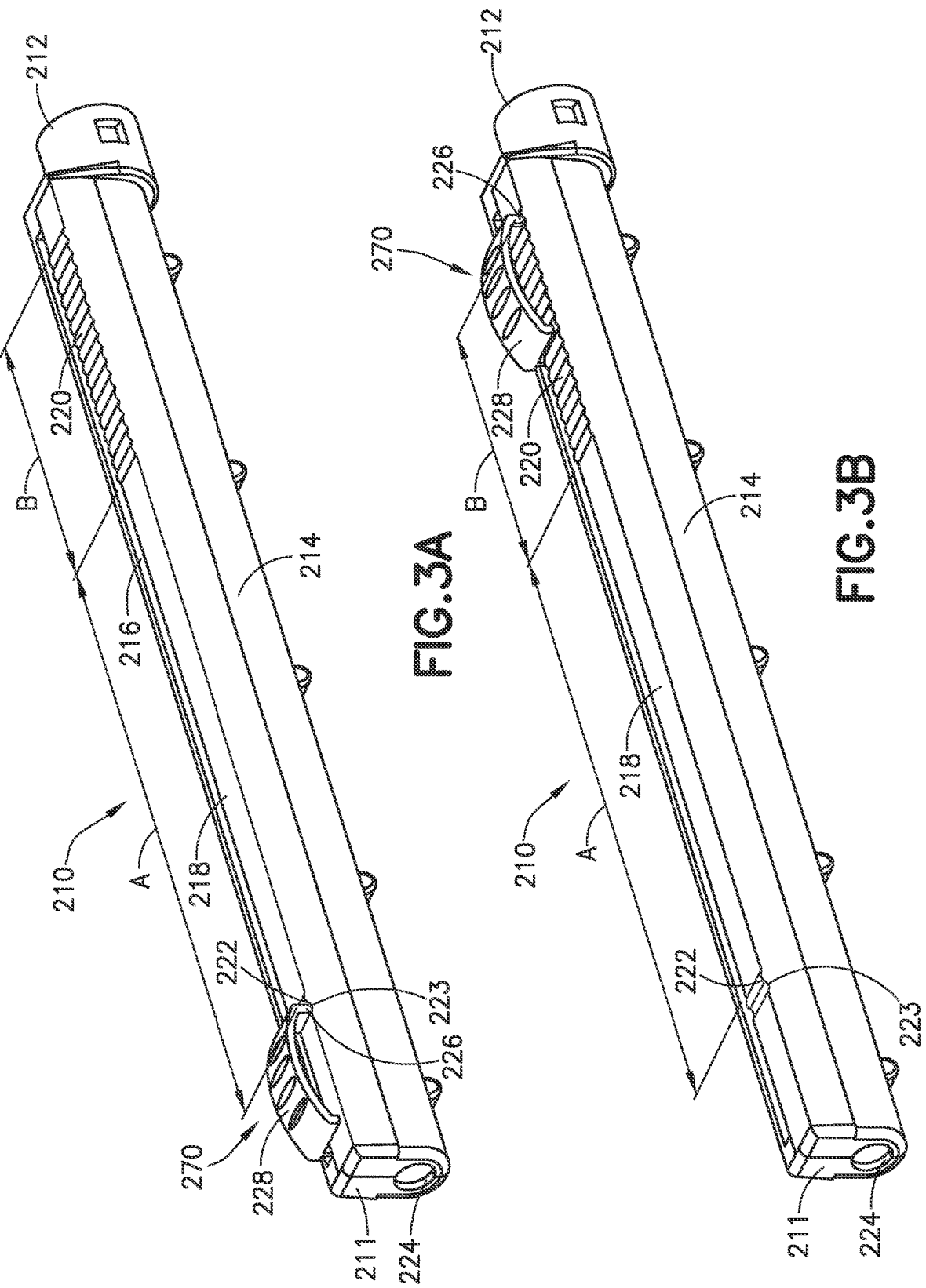
FIG. 3A is a perspective view of an introducer and actuator of a blood draw device in a first configuration in accordance with an aspect of the present disclosure.
FIG. 3B is a perspective view of the introducer and actuator of FIG. 3A in a second configuration.

Referring now to FIGS. 3A and 3B, an introducer 210 and an actuator 270 in accordance with another aspect of the present disclosure are illustrated. For ease of understanding, other features of the blood draw device such as, e.g., the catheter are not shown. However, it is to be understood that introducer 210 and actuator 270 are configured for use with a blood draw device similar to blood draw device 100 described above with respect to FIGS. 1 and 2, and, further, that the blood draw device is configured to be coupled to, e.g., a PIVC via, e.g., a lock and/or adapter.

The introducer 210 includes a proximal end portion 211 and a distal end portion 212, with the proximal end portion 211 having an opening 224 formed therein to enable fluid communication between a catheter (not shown) and, e.g., extension tubing coupled to the introducer 210. The introducer 210 includes a body 214, with the body 214 being any suitable shape, size, or configuration. For example, in some embodiments, the body 214 of introducer 210 can be an elongate member having a substantially circular or U-shaped cross-sectional shape. In some embodiments, the shape of the introducer 210 and/or one or more features or surface finishes of at least an outer surface of the introducer 210 can be arranged to increase the ergonomics of the introducer 210, which in some instances, can allow a user to manipulate the actuator 270 and hold the introducer 210 with one hand (i.e., single-handed use). Additionally and/or alternatively, body 214 of introducer 210 may be formed of two or more separate sections, with the sections being coupled via, e.g., one or more fasteners, an adhesive, welding, etc.

Introducer 210 further comprises a slot 216 extending through and along a substantial portion of a top surface of the introducer 210 between the proximal end portion 211 and the distal end portion 212. The slot 216 is configured to allow a body portion (not shown) of the actuator 270 slidably disposed within the introducer 210 to be coupled with an engagement member 228 such that movement of the engagement member 228 along the slot 216 results in corresponding movement of the body portion within the introducer 210. As such, the engagement member 228 can be engaged and/or manipulated by a user (e.g., by a finger or thumb of the user) to move the actuator 270 relative to the introducer 210. In some embodiments, the engagement member 228 can include a set of ridges and/or any suitable surface finish that can, for example, increase the grip and/or ergonomics of the actuator 270 and/or introducer 210.

Referring still to FIGS. 3A and 3B, the top surface of the introducer 210 includes a first surface portion 218 extending a length A, and a second surface portion 220 extending a length B. The first surface portion 218 extends substantially from the proximal end portion 211 to a proximal end of second surface portion 220, while the second surface portion 220 extends substantially from a distal end of the first surface portion 218 toward the distal end portion 212 of introducer 210. In some embodiments, the first surface portion 218 is substantially smooth along the length A, while the second surface portion 220 comprises a plurality of ridges or ribs extending along the length B.

Thus, when the actuator 270 is manipulated by a user across the first surface portion 218, there is minimal tactile feedback and/or vibration felt by the user through the engagement member 228 from the introducer 210. However, as the actuator 270 is manipulated distally, a downwardly-extending tab 226 of actuator 270 comes into contact with the ridges of second surface portion 220, thereby providing tactile feedback and/or vibration to the user. In this way, the user is provided with positive tactile and/or audible feedback as the actuator 270 approaches the distal end portion 212 of the introducer 210, which correlates to the point at which a distal end of the catheter/flow tube (not shown) coupled to the actuator 270 nears its intended position within the patient's vasculature. Conversely, because the first surface portion 218 is substantially smooth, the user is able to better detect tactile feedback directly from the catheter/flow tube coupled to the actuator 270 should the catheter/flow tube encounter any obstructions, obstacles, or resistance resulting through contact with valves or other vein anatomy as the actuator is manipulated along the first surface portion 218.

Additionally and/or alternatively, the introducer 210 may also include a convex protrusion 222 located near the proximal end portion 211, and a concave indentation 223 located proximally (and substantially adjacent) to the convex protrusion 222. As shown in FIG. 3A, the concave indentation 223 and convex protrusion 222 can be located so as to provide a physical "stop" for the downwardly-extending tab 226 of actuator 270. If the user wishes to manipulate actuator 270 along the introducer 210, the user must apply enough force to enable the downwardly-extending tab 226 to exit the concave indentation 223 and slide over the convex protrusion 222. With this configuration, inadvertent and/or unwanted movement of the actuator 270 along the introducer 210 can be avoided. Furthermore, the convex protrusion 222 may provide tactile and/or audible feedback to the user to indicate when the actuator 270 has entered and/or exited the first surface portion 218.

Figures 4A, 4B:
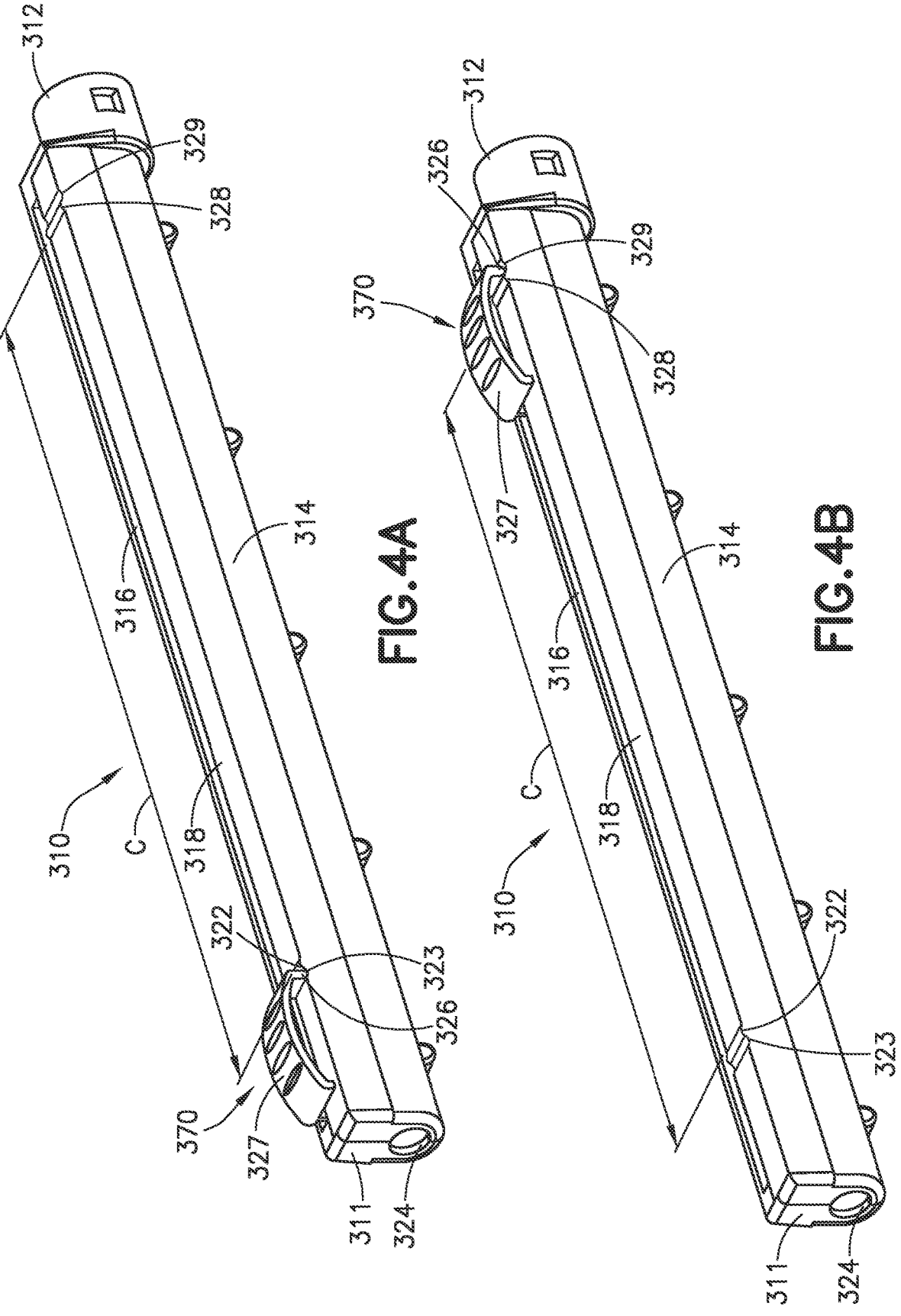
FIG. 4A is a perspective view of an introducer and actuator of a blood draw device in a first configuration in accordance with another aspect of the present disclosure.
FIG. 4B is a perspective view of the introducer and actuator of FIG. 4A in a second configuration.

Referring now to FIGS. 4A and 4B, an introducer 310 and an actuator 370 in accordance with another aspect of the present disclosure are illustrated. As with introducer 210 and actuator 270 described above with respect to FIGS. 3A and 3B, for ease of understanding, not all features of the blood draw device are shown. However, it is to be understood that introducer 310 and actuator 370 are configured for use with a blood draw device similar to blood draw device 100 described above with respect to FIGS. 1 and 2, and, further, that the blood draw device is configured to be coupled to, e.g., a PIVC via, e.g., a lock and/or adapter.

The introducer 310 includes a proximal end portion 311 and a distal end portion 312, with the proximal end portion 311 having an opening 324 formed therein to enable fluid communication between a catheter (not shown) and, e.g., extension tubing coupled to the introducer 310. The introducer 310 also includes a body 314, with the body 314 being any suitable shape, size, or configuration. In some embodiments, the body 314 of introducer 310 can be an elongate member having a substantially circular or U-shaped cross-sectional shape. In some embodiments, the shape of the introducer 310 and/or one or more features or surface finishes of at least an outer surface of the introducer 310 can be arranged to increase the ergonomics of the introducer 310 to enable a user to manipulate the actuator 370 and hold the introducer 310 with one hand (i.e., single-handed use). Additionally and/or alternatively, body 314 of introducer 310 may be formed of two or more separate sections, with the sections being coupled via, e.g., one or more fasteners, an adhesive, welding, etc.

Introducer 310 includes a slot 316 extending through and along a substantial portion of a top surface of the introducer 310 between the proximal end portion 311 and the distal end portion 312. The slot 316 is configured to allow a body portion (not shown) of the actuator 370 slidably disposed within the introducer 310 to be coupled with an engagement member 327 of the actuator 370. Thus, movement of the engagement member 327 along the slot 316 results in corresponding movement of the body portion within the introducer 310. As such, the engagement member 327 can be engaged and/or manipulated by a user (e.g., by a finger or thumb of the user) to move the actuator 370 relative to the introducer 310. In some embodiments, the engagement member 327 can include a set of ridges and/or any suitable surface finish that can, for example, increase the grip and/or ergonomics of the actuator 370 and/or introducer 310.

Referring still to FIGS. 4A and 4B, the top surface of the introducer 310 includes a surface portion 318 extending a length C. The length C extends substantially from the proximal end portion 311 to the distal end portion 312 of introducer 310. In some embodiments, the surface portion 318 is substantially smooth along the entirety of length C. Thus, when the actuator 370 is manipulated by a user across the surface portion 318, there is minimal tactile feedback and/or vibration felt by the user through the engagement member 327.

Unlike introducer 210 described above with respect to FIGS. 3A and 3B, introducer 310 does not include a top surface portion having a plurality of ridges or ribs so as to impart tactile feedback on the actuator 370 as it approaches the distal end portion 312. Rather, introducer 310 includes a pair of indentation/protrusion features positioned near the proximal end portion 311 and distal end portion 312, respectively, with these indentation/protrusion features providing both a physical stop for the actuator 370 and tactile feedback to the user.

Specifically, the introducer 310 includes include a first convex protrusion 322 located near the proximal end portion 311, and a first concave indentation 323 located proximally (and substantially adjacent) to the first convex protrusion 322. As shown in FIG. 4A, the first concave indentation 323 and first convex protrusion 322 can be located so as to provide a physical "stop" for a downwardly-extending tab 326 of actuator 370. If the user wishes to manipulate actuator 370 along the introducer 310, the user must apply enough force to enable the downwardly-extending tab 326 to exit the first concave indentation 323 and slide over the first convex protrusion 322. With this configuration, inadvertent and/or unwanted movement of the actuator 370 along the introducer 310 can be avoided.

Similarly, the introducer 310 also includes a second convex protrusion 328 located near the distal end portion 312, along with a second concave indentation 329 located distally (and substantially adjacent) to the second convex protrusion 328. Referring to FIG. 4B, the second concave indentation 329 and second convex protrusion 328 are provided so as to act as a physical "stop" for the downwardly-extending tab 326 of actuator 370 relative to the distal end portion 312. Thus, if the user wishes to manipulate actuator 370 to its farthest distal position along the introducer 310, the user must apply enough force to enable the downwardly-extending tab 326 to slide over the second convex protrusion 328 and into the second concave indentation 329. Likewise, if the user wishes to manipulate the actuator 370 from this farthest distal position, a proximally-directed force must be applied to the actuator 370 to overcome the second convex protrusion 328. With this configuration, inadvertent and/or unwanted movement of the actuator 370 along the introducer 310 can be avoided. Furthermore, the first convex protrusion 322 and second convex protrusion 328 may provide tactile and/or audible feedback to the user to indicate when the actuator 370 has reached the respective proximal and distal limits of the introducer 310. However, because the surface portion 318 is substantially smooth, the user is able to better detect tactile feedback directly from the catheter/flow tube coupled to the actuator 370 should the catheter/flow tube encounter any obstructions, obstacles, or resistance resulting through contact with valves or other vein anatomy as the actuator 370 is manipulated along the surface portion 318.

Figures 5A, 5B:
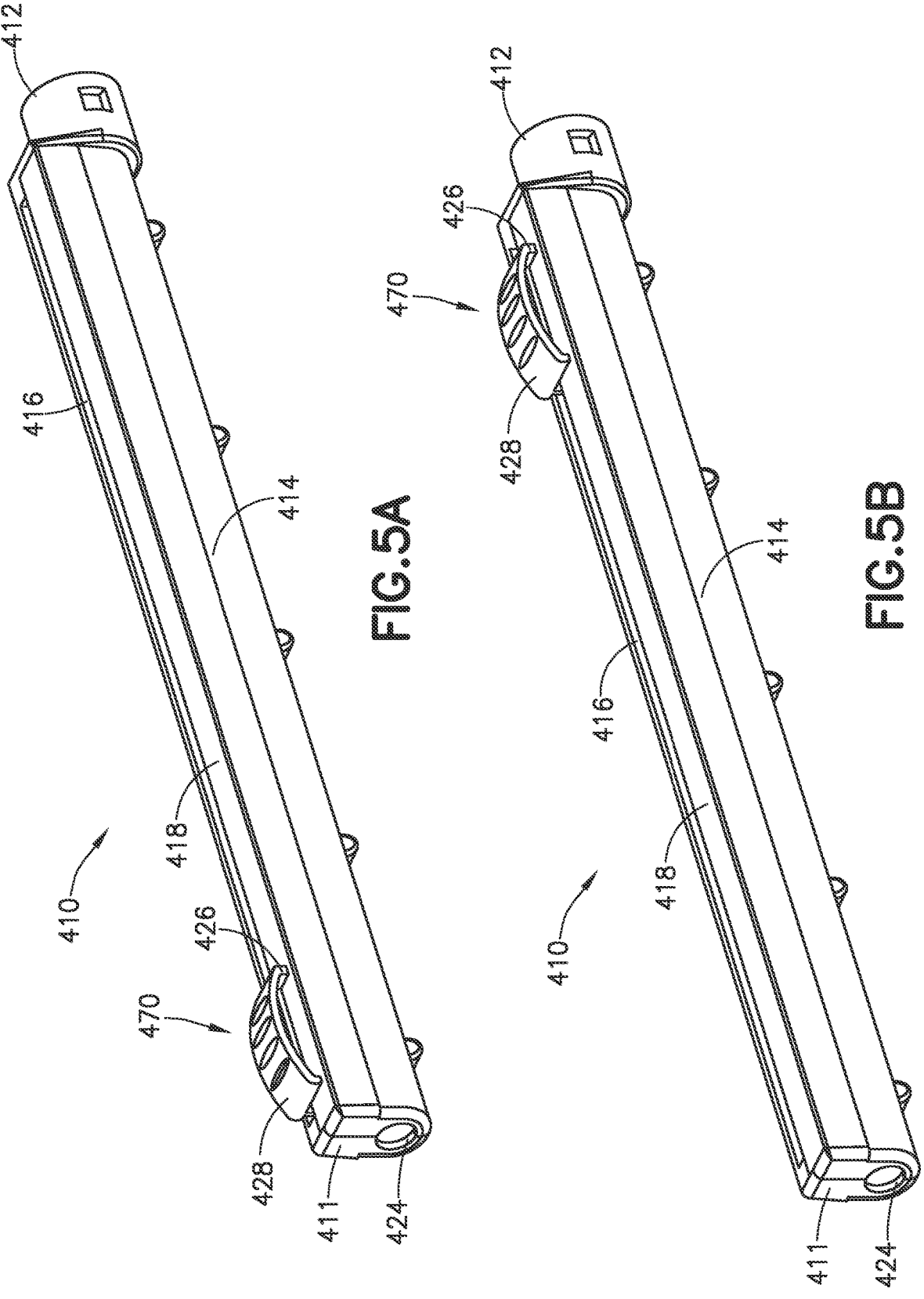
FIG. 5A is a perspective view of an introducer and actuator of a blood draw device in a first configuration in accordance with another aspect of the present disclosure.
FIG. 5B is a perspective view of the introducer and actuator of FIG. 5A in a second configuration.

Next, referring to FIGS. 5A and 5B, an introducer 410 and actuator 470 in accordance with another aspect of the present disclosure is illustrated. As described above with respect to FIGS. 3A-4B, the respective introducers 210, 310 included features located on a top surface thereof configured to provide the user with tactile feedback as the actuators 270, 370 were manipulated thereon. However, due to the downward force that a user applies with their thumb or finger on the respective engagement members 228, 327 of the actuators 270, 370, such features on the top surface of the introducer may not be ideal, as the combination of downward and sideways forces applied to the engagement member 228, 327 may result in undesirable levels of resistance and/or vibration when operating the actuator and introducer. Accordingly, as will be described in further detail below, introducer 410 and actuator 470 are configured such that the tactile feedback features are provided on an upper interior surface of the introducer 410, which may actually reduce the level of resistance and/or vibration upon increased downward force applied to the actuator 470.

As shown in FIGS. 5A and 5B, introducer 410 and actuator 470 are configured for use with a blood draw device similar to blood draw device 100 described above with respect to FIGS. 1 and 2, and, further, that the blood draw device is configured to be coupled to, e.g., a PIVC via, e.g., a lock and/or adapter. The introducer 410 includes a proximal end portion 411 and a distal end portion 412, with the proximal end portion 411 having an opening 424 formed therein to enable fluid communication between a catheter (not shown) and, e.g., extension tubing coupled to the introducer 410.

The introducer 410 also includes a body 414, with the body 414 being any suitable shape, size, or configuration. In some embodiments, the body 414 of introducer 410 can be an elongate member having a substantially circular or U-shaped cross-sectional shape. In some embodiments, the shape of the introducer 410 and/or one or more features or surface finishes of at least an outer surface of the introducer 410 can be arranged to increase the ergonomics of the introducer 410 to enable a user to manipulate the actuator 470 and hold the introducer 410 with one hand (i.e., single-handed use). Additionally and/or alternatively, body 414 of introducer 410 may be formed of two or more separate sections, with the sections being coupled via, e.g., one or more fasteners, an adhesive, welding, etc.

The introducer 410 includes a slot 416 extending through and along a substantial portion of a top surface of the introducer 410 between the proximal end portion 411 and the distal end portion 412. The slot 416 is configured to allow a body portion (not shown) of the actuator 470 slidably disposed within the introducer 410 to be coupled with an engagement member 428 of the actuator 470. Thus, movement of the engagement member 428 along the slot 416 results in corresponding movement of the body portion within the introducer 410. As such, the engagement member 428 can be engaged and/or manipulated by a user (e.g., by a finger or thumb of the user) to move the actuator 470 relative to the introducer 410. In some embodiments, the engagement member 428 can include a set of ridges and/or any suitable surface finish that can, for example, increase the grip and/or ergonomics of the actuator 470 and/or introducer 410.

Figure 6A:
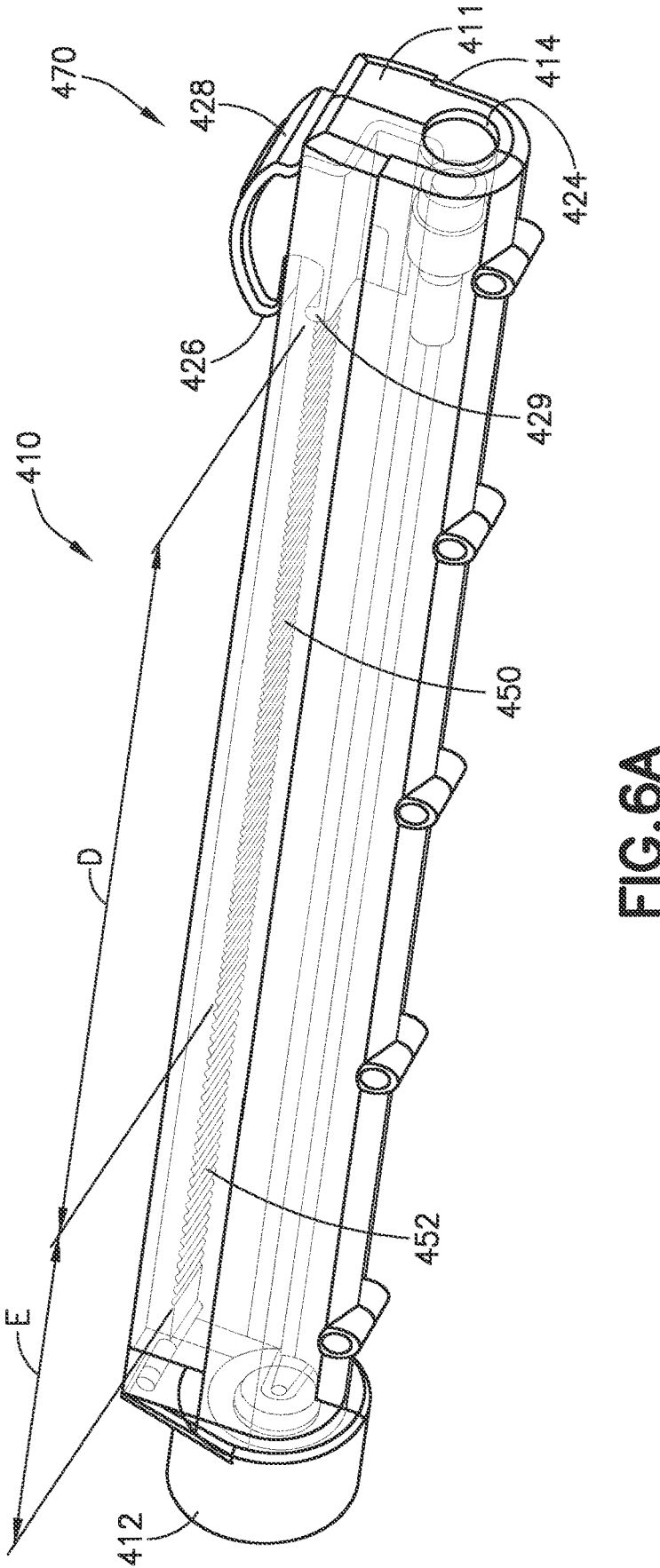
FIG. 6A is a partial perspective view of the introducer and actuator of FIGS. 5A and 5B in a first configuration in accordance with an aspect of the present disclosure.

The body 414 of introducer 410 also includes a top surface portion 418 running substantially from the proximal end portion 411 to the distal end portion 412. However, the top surface portion 418 does not include ridges or other features to provide tactile feedback to the user via the actuator 470. Rather, referring to FIGS. 6A and 6B, the introducer 410 includes interior upper surfaces 450, 452 having a plurality of ridges or ribs formed thereon. More specifically, a first interior upper surface 450 extends a length D within the introducer 410, while a second interior upper surface 452 extends a length E within the introducer 410. The first interior upper surface 450 includes a plurality of ridges having a first size, while the second interior upper surface 452 includes a plurality of ridges having a second size larger than the first size. Thus, when the actuator 470 is manipulated by a user across the top surface portion 418, an upwardly-extending tab 429 of actuator 470 comes into contact with the ridges of both the first interior upper surface 450 and the second interior upper surface 452, thereby providing varying tactile feedback and/or vibration to the user. Due to the larger size of the plurality of ridges of second interior upper surface 452 as compared to those of the first interior upper surface 450, the tactile feedback felt (and/or audible feedback heard) by the user through actuator 470 increases as the actuator 470 transitions from the ridges of first interior upper surface 450 to those of the second interior upper surface 452. In this way, the user is provided with positive tactile and/or audible feedback as the actuator 470 approaches the distal end portion 412 of the introducer 410, which correlates to the point at which a distal end of the catheter/flow tube (not shown) coupled to the actuator 470 nears its intended position within the patient's vasculature.

Figure 6B:
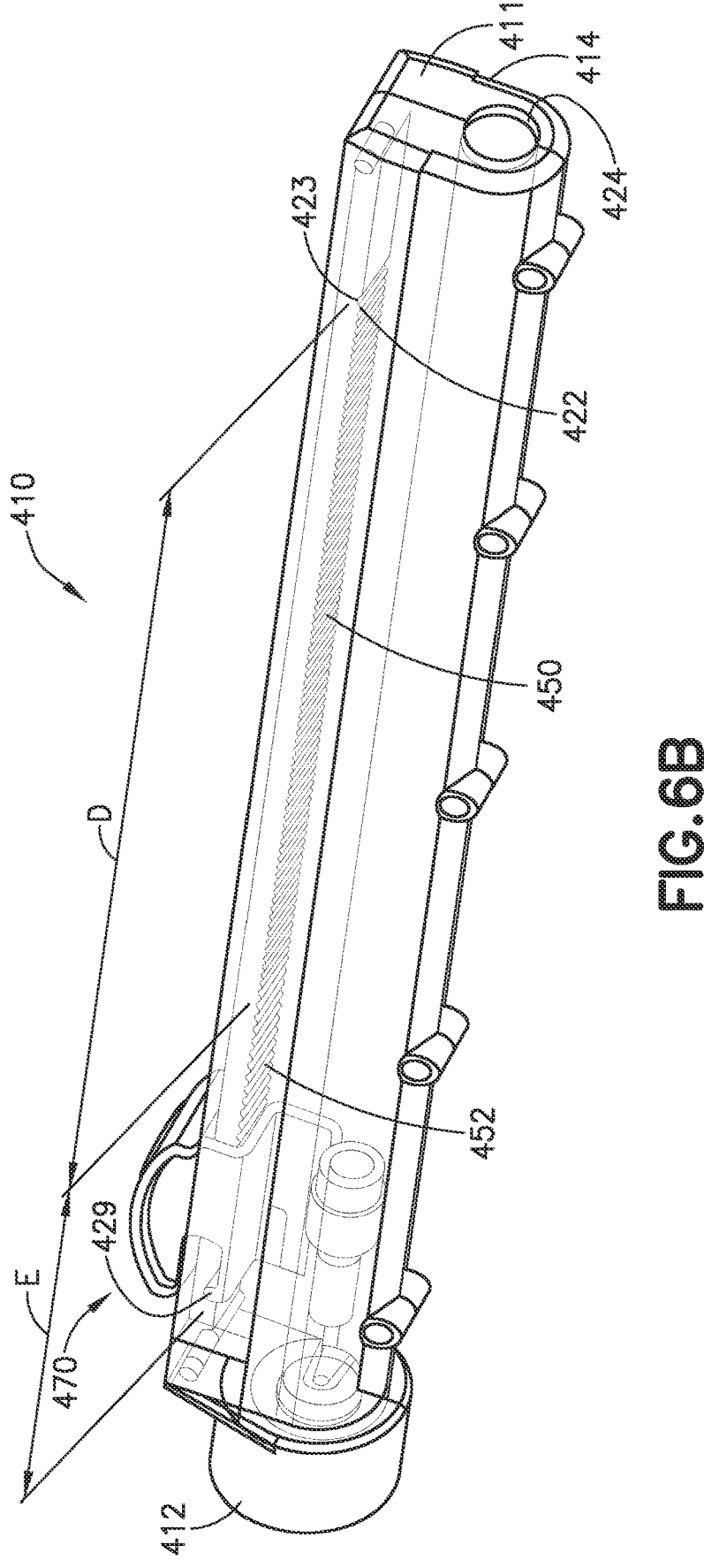
FIG. 6B is a partial perspective view of the introducer and actuator of FIGS. 5A and 5B in a second configuration in accordance with an aspect of the present disclosure.

Additionally and/or alternatively, the introducer 410 may also include a convex protrusion 422 located on the upper interior surface near the proximal end portion 411, and a concave indentation 423 located proximally (and substantially adjacent) to the convex protrusion 422. As shown in FIG. 6B, the concave indentation 423 and convex protrusion 422 can be located so as to provide a physical "stop" for the upwardly-extending tab 429 of actuator 470. If the user wishes to manipulate actuator 470 along the introducer 410, the user must apply enough force to enable the upwardly-extending tab 429 to exit the concave indentation 423 and slide over the convex protrusion 422. With this configuration, inadvertent and/or unwanted movement of the actuator 470 along the introducer 410 can be avoided. Furthermore, the convex protrusion 422 may provide tactile and/or audible feedback to the user to indicate when the actuator 470 has entered and/or exited the first interior upper surface 450.

Furthermore, as is shown in FIGS. 5A-6A, actuator 470 also includes a downwardly-extending tab 426. Accordingly, in some embodiments, the introducer may be provided with one or more additional features on the top surface portion 418 configured to interact with the downwardly-extending tab 426 so as to provide, e.g., additional tactile feedback, etc.

Figure 7A:
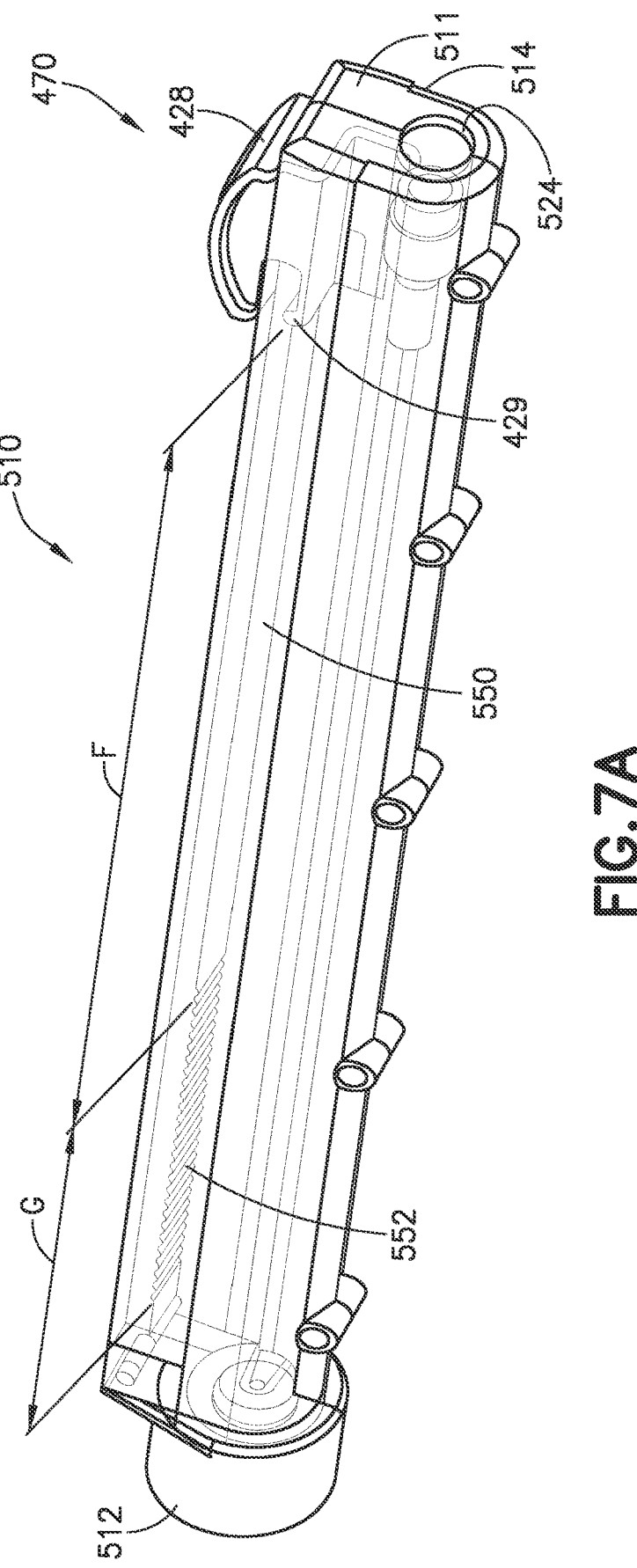
FIG. 7A is a partial perspective view of the introducer and actuator of FIGS. 5A and 5B in a first configuration in accordance with another aspect of the present disclosure.
Figure 7B:
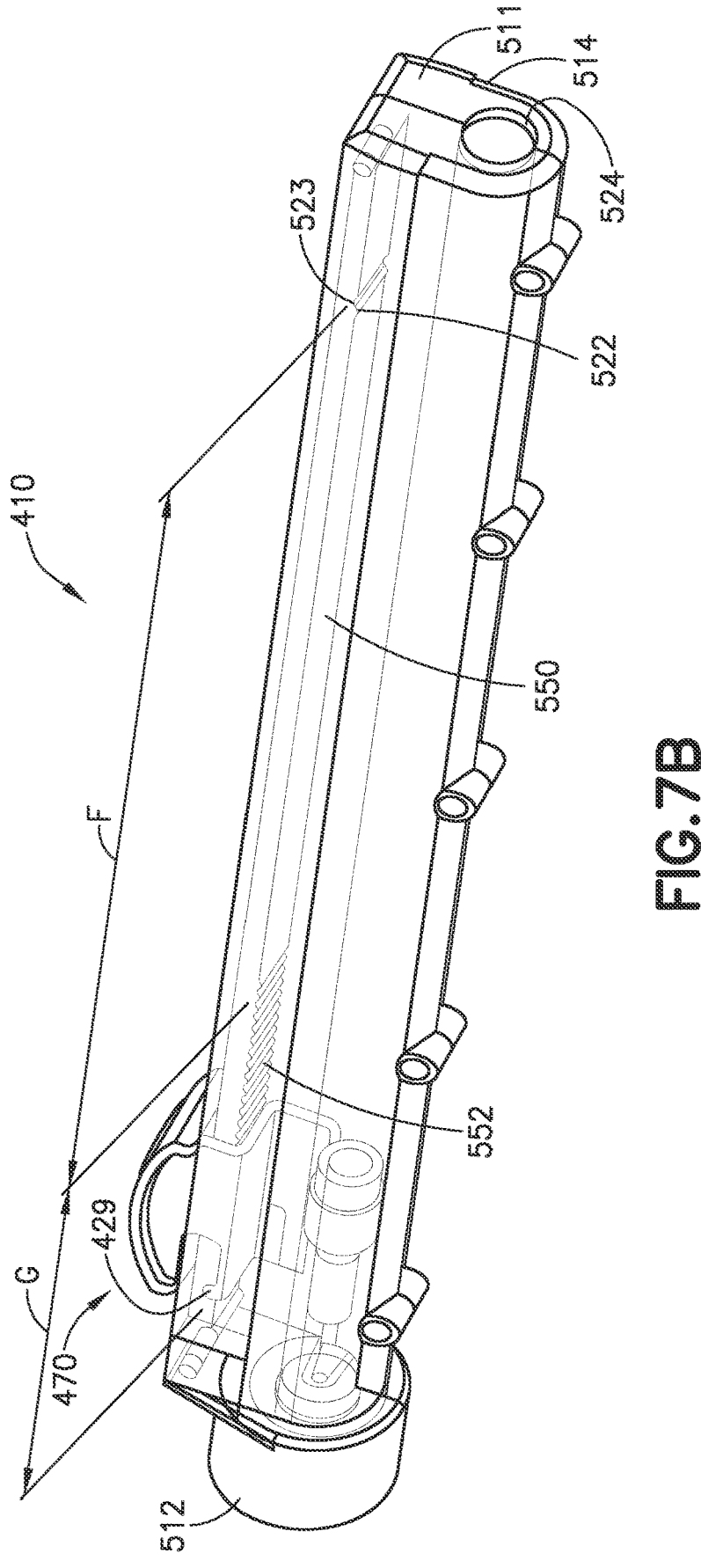
FIG. 7B is a partial perspective view of the introducer and actuator of FIGS. 5A and 5B in a second configuration in accordance with another aspect of the present disclosure.

Next, referring to FIGS. 7A and 7B, an introducer 510 in accordance with another aspect of the present disclosure is illustrated. Externally, introducer 510 is substantially similar to introducer 410 described above with respect to FIGS. 5A-6B, and is configured to be usable with actuator 470. That is, introducer 510 includes a proximal end portion 511 and a distal end portion 512, with the proximal end portion 511 having an opening 524 formed therein to enable fluid communication between a catheter (not shown) and, e.g., extension tubing coupled to the introducer 510. The introducer 510 also includes a body 514, with the body 514 being any suitable shape, size, or configuration. In some embodiments, the body 514 of introducer 510 can be an elongate member having a substantially circular or U-shaped cross-sectional shape.

However, unlike introducer 410, which includes two distinct sections of ridges or ribs on an interior upper surface thereof, the introducer 510 includes interior upper surfaces 550, 552, but only one of the two interior upper surfaces include a plurality of ridges or ribs. More specifically, a first interior upper surface 550 extends a length F within the introducer 510, while a second interior upper surface 552 extends a length G within the introducer 510. The first interior upper surface 550 is substantially smooth along the length F, while the second interior upper surface 552 includes a plurality of ridges extending along the length G. Thus, when the actuator 470 is manipulated by a user across the top surface portion of the introducer 510, the upwardly-extending tab 429 of actuator 470 travels across the first interior upper surface 550 with minimal (if any) resistance. However, when the actuator 470 reaches the second interior upper surface 552, the plurality of ridges of the second interior upper surface 552 provide tactile feedback and/or vibration to the user. In this way, the user is provided with positive tactile and/or audible feedback as the actuator 470 approaches the distal end portion 512 of the introducer 510, which correlates to the point at which a distal end of the catheter/flow tube (not shown) coupled to the actuator 470 nears its intended position within the patient's vasculature. However, because the first interior upper surface 550 is substantially smooth, the user is able to better detect tactile feedback directly from the catheter/flow tube coupled to the actuator 470 should the catheter/flow tube encounter any obstructions, obstacles, or resistance resulting through contact with valves or other vein anatomy as the actuator is manipulated along the length F of the first interior upper surface 550.

Additionally and/or alternatively, referring to FIG. 7B, the introducer 510 may also include a convex protrusion 522 located on the upper interior surface near the proximal end portion 511, and a concave indentation 523 located proximally (and substantially adjacent) to the convex protrusion 522. The concave indentation 523 and convex protrusion 522 can be located so as to provide a physical "stop" for the upwardly-extending tab 429 of actuator 470. If the user wishes to manipulate actuator 470 along the introducer 510, the user must apply enough force to enable the upwardly-extending tab 429 to exit the concave indentation 523 and slide over the convex protrusion 522. With this configuration, inadvertent and/or unwanted movement of the actuator 470 along the introducer 510 can be avoided. Furthermore, the convex protrusion 522 may provide tactile and/or audible feedback to the user to indicate when the actuator 570 has entered and/or exited the first interior upper surface 550.

Figure 8A:
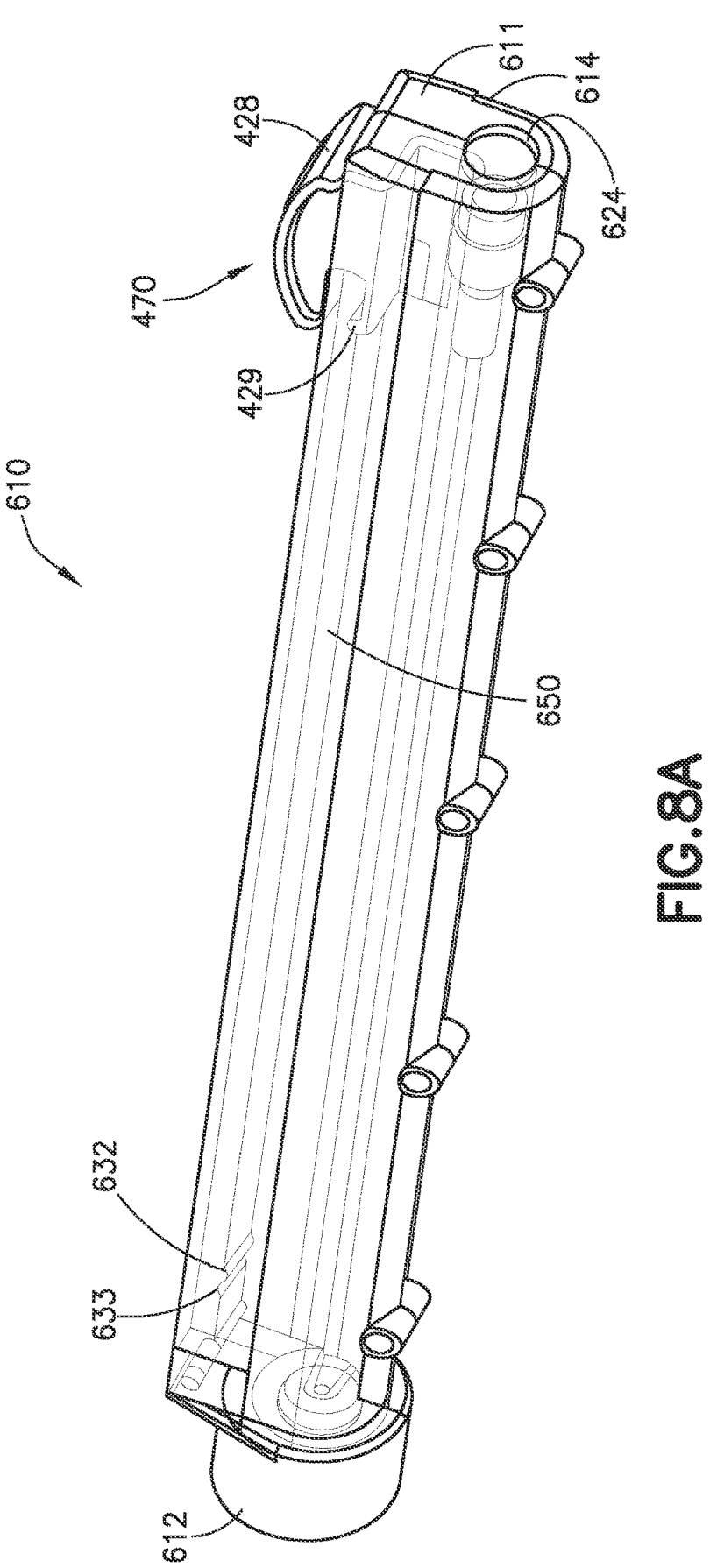
FIG. 8A is a partial perspective view of the introducer and actuator of FIGS. 5A and 5B in a first configuration in accordance with another aspect of the present disclosure.
Figure 8B:
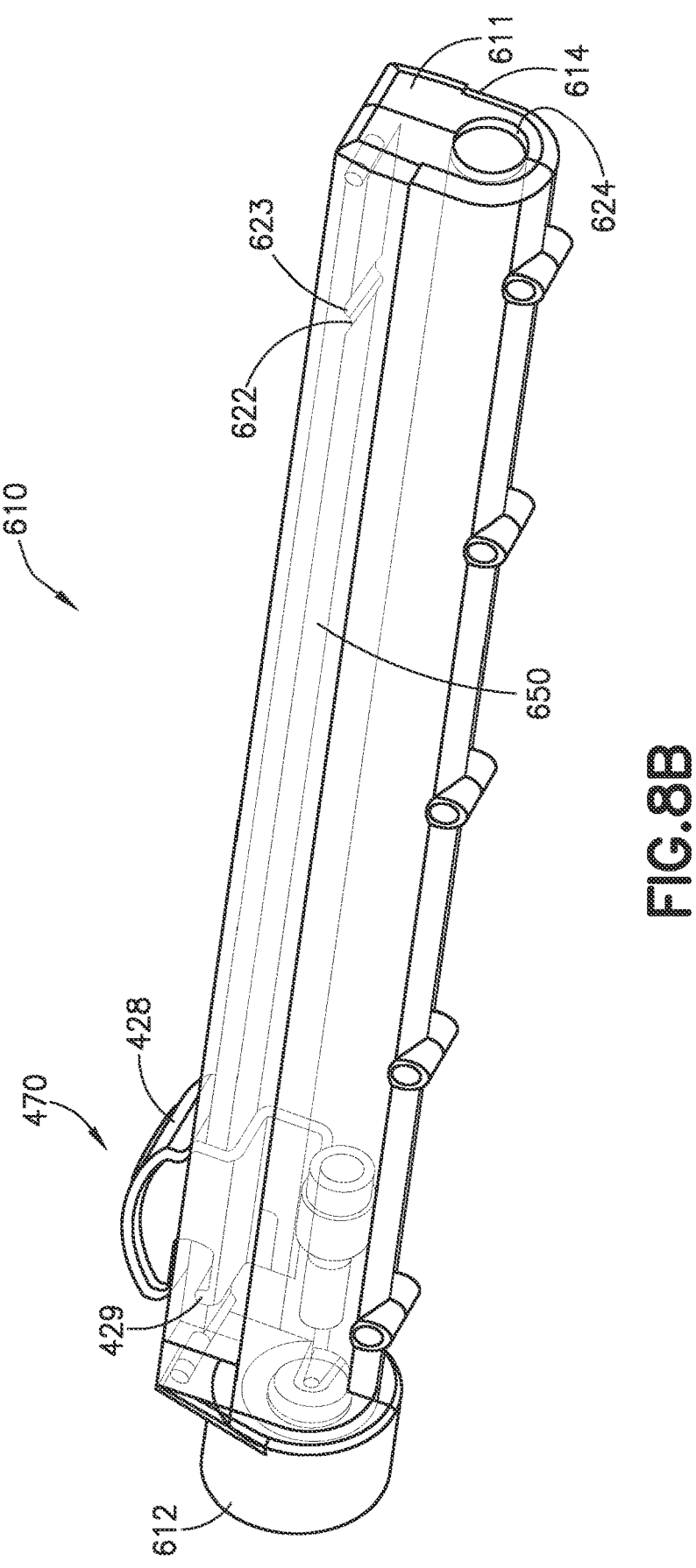
FIG. 8B is a partial perspective view of the introducer and actuator of FIGS. 5A and 5B in a second configuration in accordance with another aspect of the present disclosure

Next, referring to FIGS. 8A and 8B, an introducer 610 in accordance with another aspect of the present disclosure is illustrated Like introducer 510 described above with respect to FIGS. 7A and 7B, introducer 610 is substantially similar to introducer 410 described above with respect to FIGS. 5A-6B, and is configured to be usable with actuator 470. Introducer 610 includes a proximal end portion 611 and a distal end portion 612, with the proximal end portion 611 having an opening 624 formed therein to enable fluid communication between a catheter (not shown) and, e.g., extension tubing coupled to the introducer 610. The introducer 610 also includes a body 614, with the body 614 being any suitable shape, size, or configuration. In some embodiments, the body 614 of introducer 610 can be an elongate member having a substantially circular or U-shaped cross-sectional shape.

However, unlike both introducer 410 and introducer 510, introducer 610 does not include a plurality of adjacent ridges or ribs on any surface thereof to provide tactile and/or audible feedback. Instead, introducer 610 includes an interior underside surface 650 that is substantially smooth along its entire length. At a proximal end of the interior underside surface 650, introducer 610 includes a first convex protrusion 622 located near the proximal end portion 611, and a first concave indentation 623 located proximally (and substantially adjacent) to the first convex protrusion 622. The first concave indentation 623 and first convex protrusion 622 can be located so as to provide a physical "stop" for upwardly-extending tab 429 of actuator 470. If the user wishes to manipulate actuator 470 along the introducer 610, the user must apply enough force to enable the upwardly-extending tab 429 to exit the first concave indentation 623 and slide over the first convex protrusion 622. With this configuration, inadvertent and/or unwanted movement of the actuator 470 along the introducer 610 can be avoided.

Additionally, the introducer 610 also includes a second convex protrusion 632 located near the distal end portion 612, along with a second concave indentation 633 located distally (and substantially adjacent) to the second convex protrusion 632. Referring to FIG. 8B, the second concave indentation 633 and second convex protrusion 632 are provided so as to act as a physical "stop" for the upwardly-extending tab 429 of actuator 470 relative to the distal end portion 612. Thus, if the user wishes to manipulate actuator 470 to its farthest distal position along the introducer 640, the user must apply enough force to enable the upwardly-extending tab 429 to slide over the second convex protrusion 632 and into the second concave indentation 633. Likewise, if the user wishes to manipulate the actuator 470 from this farthest distal position, a proximally-directed force must be applied to the actuator 470 to overcome the second convex protrusion 632.

With this configuration, inadvertent and/or unwanted movement of the actuator 470 along the introducer 610 can be avoided. Furthermore, the first convex protrusion 622 and second convex protrusion 632 may provide tactile and/or audible feedback to the user to indicate when the actuator 470 has reached the respective proximal and distal limits of the introducer 610. However, because the surface portion interior underside surface 650 is substantially smooth along its length between the respective convex protrusions 622, 632, the user is able to better detect tactile feedback directly from the catheter/flow tube coupled to the actuator 470 should the catheter/flow tube encounter any obstructions, obstacles, or resistance resulting through contact with valves or other vein anatomy as the actuator 470 is manipulated along the interior underside surface 650.

Figure 9:
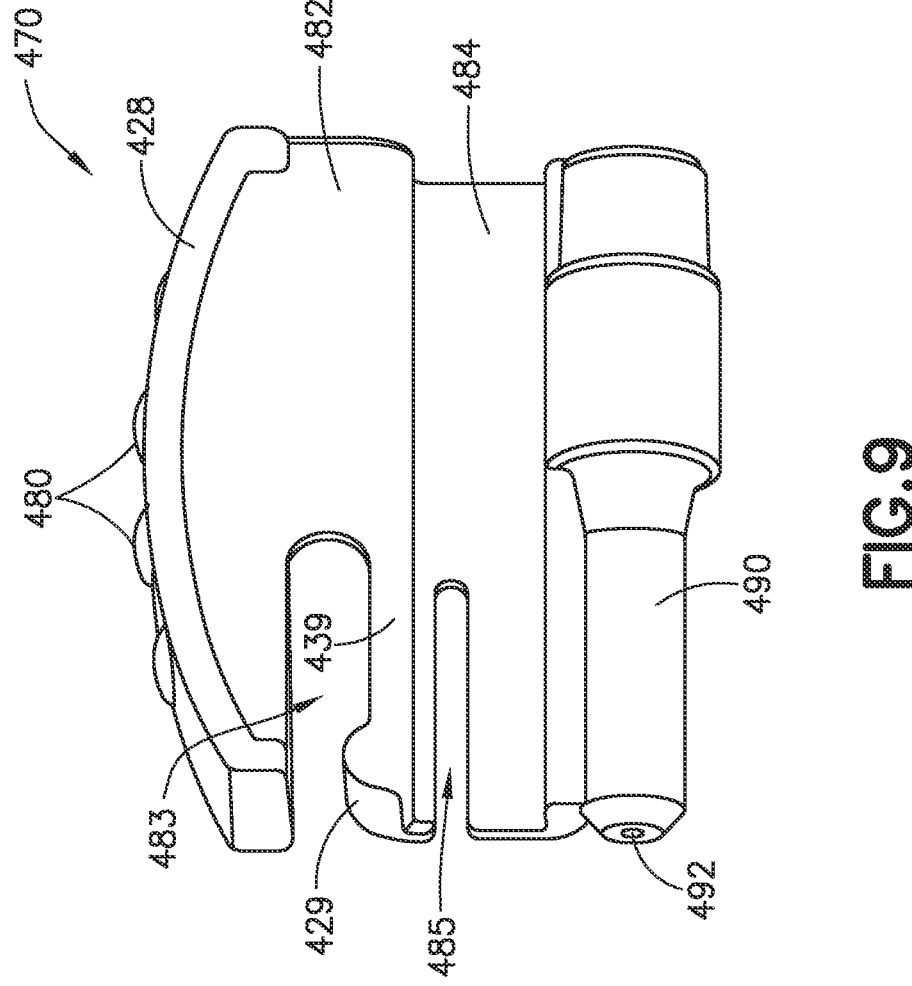
FIG. 9 is a perspective view of an actuator in accordance with an aspect of the present disclosure.

Referring now to FIG. 9, specific features of actuator 470 are shown in greater detail. Actuator 470 includes an upper portion 482 and a lower portion 490, with a wall 484 extending therebetween. Part of the upper portion 482 of the actuator 470 may be at least partially disposed within the an inner volume defined through and below the slot of the introducer, while the lower portion 490 may be entirely disposed within another portion of the inner volume of the introducer. The upper portion 482 of the actuator 470 includes the engagement member 428. The arrangement of the actuator 470 is such that the engagement member 428 is disposed outside of the introducer, while the rest of upper portion 482 is within the an inner volume defined by the introducer. As such, the engagement member 428 can be engaged and/or manipulated by a user (e.g., by a finger or thumb of the user) to move the actuator 470 relative to the introducer. In some embodiments, the engagement member 428 can include a set of ridges 480 and/or any suitable surface finish that can, for example, increase the ergonomics of the actuator 470.

As shown, the lower portion 490 defines an opening 492, wherein opening 492 may be configured to receive a portion of at least one catheter of the blood draw device. In some embodiments, a proximal end portion of a first catheter can form a friction fit with an inner surface of the lower portion 490 of the actuator 470 when the proximal end portion is disposed in the opening 492, while a distal end portion of a second catheter can form a friction fit with an inner surface of the lower portion 490 of the actuator 470 when the distal end portion is disposed in the opening 492. As such, the first catheter and the second catheter can be maintained in a fixed position relative to the actuator 470 and thus, move concurrently with the actuator 470 as the actuator 470 is moved relative to the introducer.

Referring still to FIG. 9, the upwardly-extending tab 429 of actuator 470 is positioned on an arm member 439, with arm member 439 extending between a first gap 483 formed in the upper portion 482 and a second gap 485 formed in the wall 484. In this way, the arm member 439 (and, thus, the upwardly-extending tab 429) may cantilever, thereby allowing for easier movement of the upwardly-extending tab 429 of actuator 470 across a ridged surface of the introducer. As such, the user may be provided with tactile and/or audible feedback from the actuator 470, but movement of the actuator 470 is not greatly impeded by the plurality of ridges or other features formed on and/or within the introducer.

Figure 10:
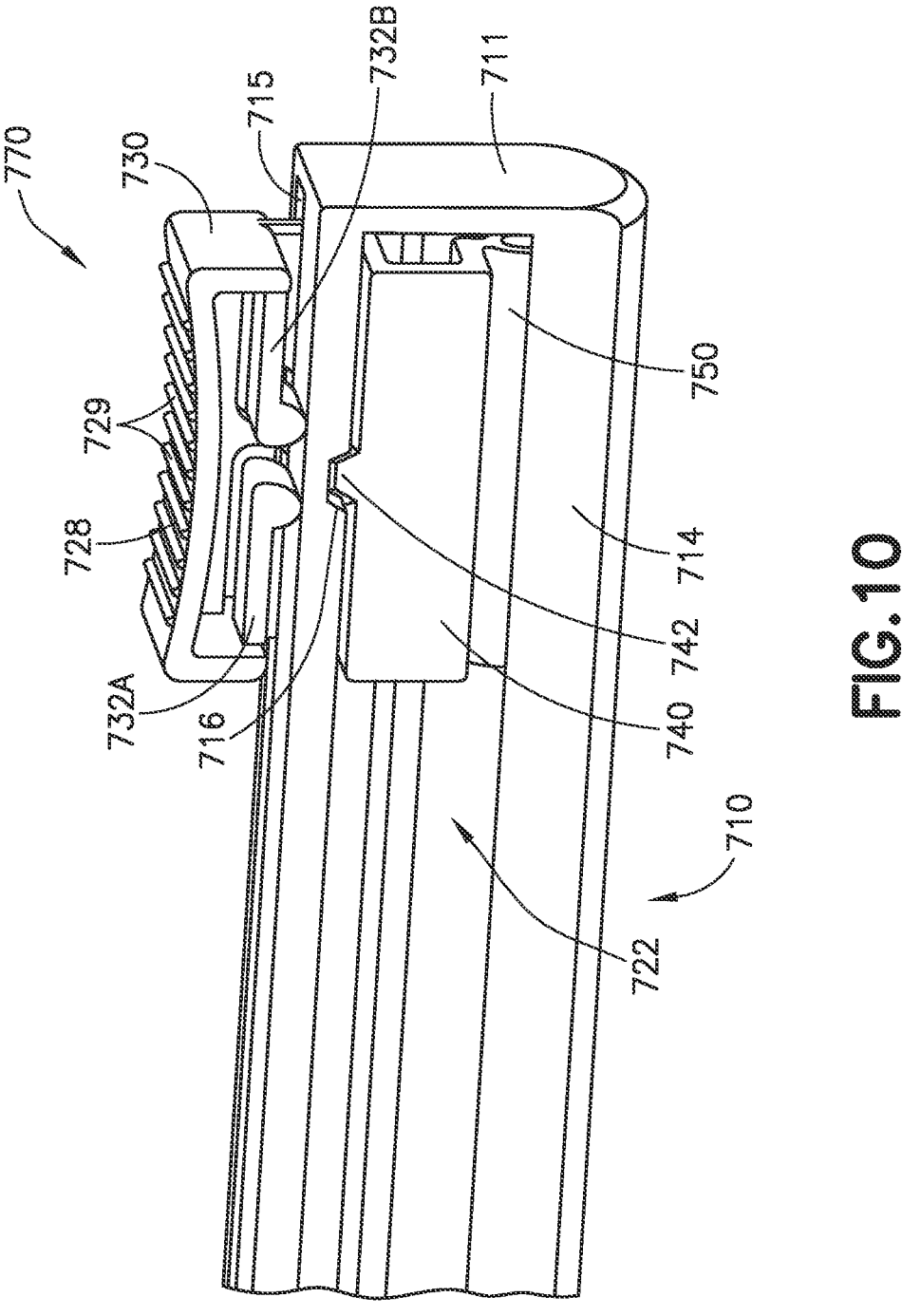
FIG. 10 is a partial perspective view of an introducer and actuator of a blood draw device in accordance with another aspect of the present disclosure.

Next, referring to FIG. 10, an introducer 710 and an actuator 770 in accordance with another embodiment of the present disclosure is shown. Introducer 710 includes a proximal end portion 711 and a distal end portion (not shown). While not shown in FIG. 10, it is to be understood that proximal end portion 711 may have an opening formed therein to enable fluid communication between a catheter (not shown) and, e.g., extension tubing coupled to the introducer 710. The introducer 710 also includes a body 714, with the body 714 being any suitable shape, size, or configuration. Similar to the introducers described above with respect to FIGS. 3A-6B, introducer 710 includes a slot 715 formed along a top surface thereof, with the slot 715 extending substantially along an entire length of the introducer 710. Furthermore, introducer 710 includes an interior space 722 formed therein, with the interior space 722 configured to slidably receive a lower portion of the actuator 770, as will be described in further detail below. The introducer 710 also may include at least one detent 716 formed on an interior surface thereof. As will be described in further detail below, the at least one detent 716 is configured to interact with a corresponding projection of the actuator 770 in order to restrict/resist movement of the actuator 770 in certain positions relative to the introducer 710.

The actuator 770 includes an upper portion 730 and a lower portion 750, with a wall 740 extending therebetween. Part of the upper portion 730 of the actuator 770 may be at least partially disposed within the an inner volume defined through and below the slot 715 of the introducer 710, while the lower portion 750 and/or the wall 740 may be entirely disposed within the interior space 722 of the introducer 710.

The upper portion 730 of the actuator 770 includes an engagement member 728. The arrangement of the actuator 770 is such that the engagement member 728 is disposed outside of the introducer 710. As such, the engagement member 728 can be engaged and/or manipulated by a user (e.g., by a finger or thumb of the user) to move the actuator 770 relative to the introducer. In some embodiments, the engagement member 728 can include a set of ridges 729 and/or any suitable surface finish that can, for example, increase the ergonomics of the actuator 770.

Additionally, actuator 770 includes a spring member configured to selectively engage (and disengage) a projection 742 extending upward from the wall 740 of actuator 770 with the detent 716 of the introducer 710. Specifically, as shown in FIG. 10, the spring member may be in the form of a leaf spring formed by respective arms 732A, 732B. The user may press downward on the engagement member 728, which deflects the arms 732A, 732B such that the projection 742 becomes clear of the detent 716, thereby allowing actuator 770 to move linearly along the introducer 710 relative to the slot 715. Conversely, when a user releases the downward pressure upon the engagement member 728, the arms 732A, 732B may force the projection 742 upward such that it engages with the detent 716, thereby restricting linear movement of the actuator 770.

While not shown in FIG. 10, it is to be understood that introducer 710 may include more than one detent for engagement. For example, the distal end portion of introducer 710 may include a second detent signifying a distal limit of travel for the actuator 770. Furthermore, it is to be understood that the spring member of the actuator 770 is not limited to a leaf spring such as that shown in FIG. 10, but may be any other suitable spring type such as, e.g., one or more coil springs, one or more elastomeric springs, etc.

Figures 11A, 11B:
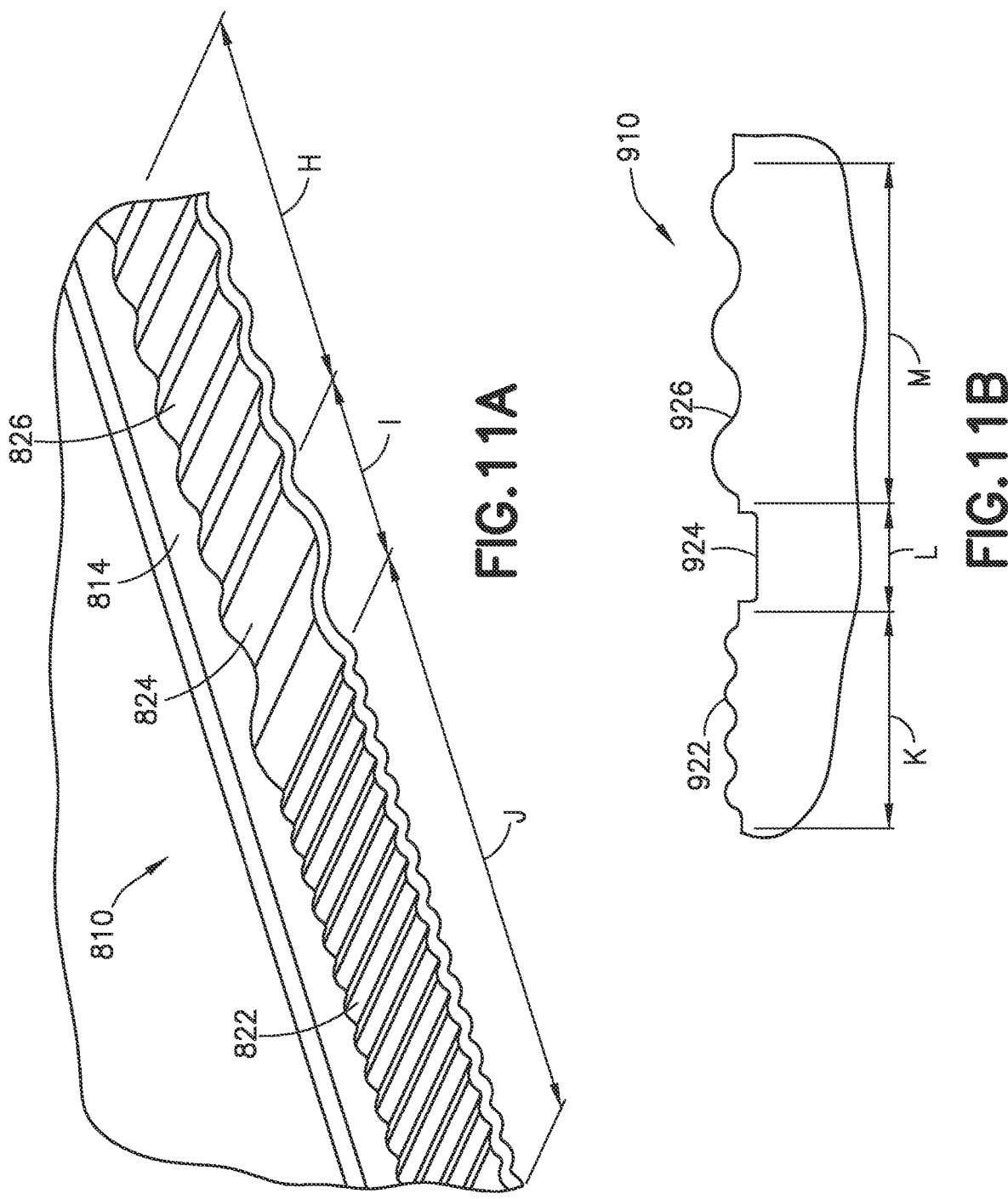
FIG. 11A is a partial perspective view of an introducer of a blood draw device in accordance with another aspect of the present disclosure.
FIG. 11B is a side profile view of a portion of an introducer of a blood draw device in accordance with another aspect of the present disclosure.

Referring now to FIGS. 11A and 11B, variations of a ridge pattern for use on an introducer to provide tactile and/or audible feature in accordance with other aspects of the present disclosure are shown. Specifically, referring to FIG. 11A, an introducer 810 is shown having a top surface 814, with the top surface 814 having a plurality of ridges extending at least partially thereon. The plurality of ridges are divided into a first ridge portion 822 having a length J, a second ridge portion 824 having a length I, and a third ridge portion 826 having a length H. The second ridge portion 824, which is positioned between the first ride portion 822 and the third ridge portion 826, may have the largest ridges, yet may have the shortest length. As such, second ridge portion 824 may provide the user with more substantial and discernable tactile feedback when the transition point between the smaller ridges of first ridge portion 822 and the larger ridges of the third ridge portion 826 is reached.

Similarly, referring to FIG. 11B, a profile view of the ridges of an introducer 910 are shown. The plurality of ridges are divided into a first ridge portion 922 having a length K, a substantially square-cut transition point 924 having a length L, and a second ridge portion 926 having a length M. The square-cut transition point 924, which is positioned between the first ridge portion 922 and the second ridge portion 926, provides for an easily discernable transition point between the different portions of the introducer, providing for clearer tactile feedback when the transition point between the smaller ridges of first ridge portion 922 and the larger ridges of the second ridge portion 926 is reached.

Figure 12:
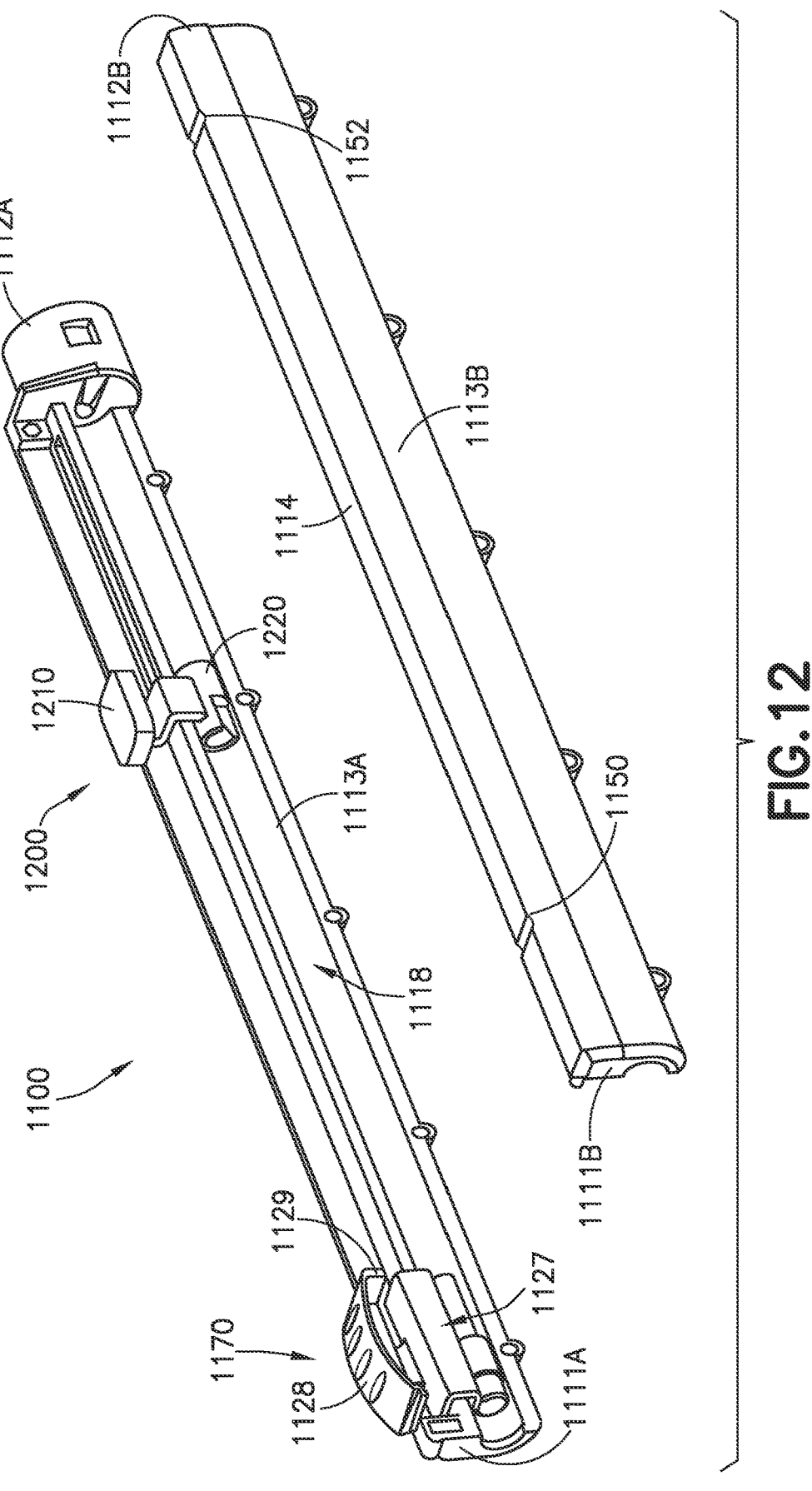
FIG. 12 is an exploded perspective view of an introducer and actuator of a blood draw device in accordance with another aspect of the present disclosure.
Figure 13:
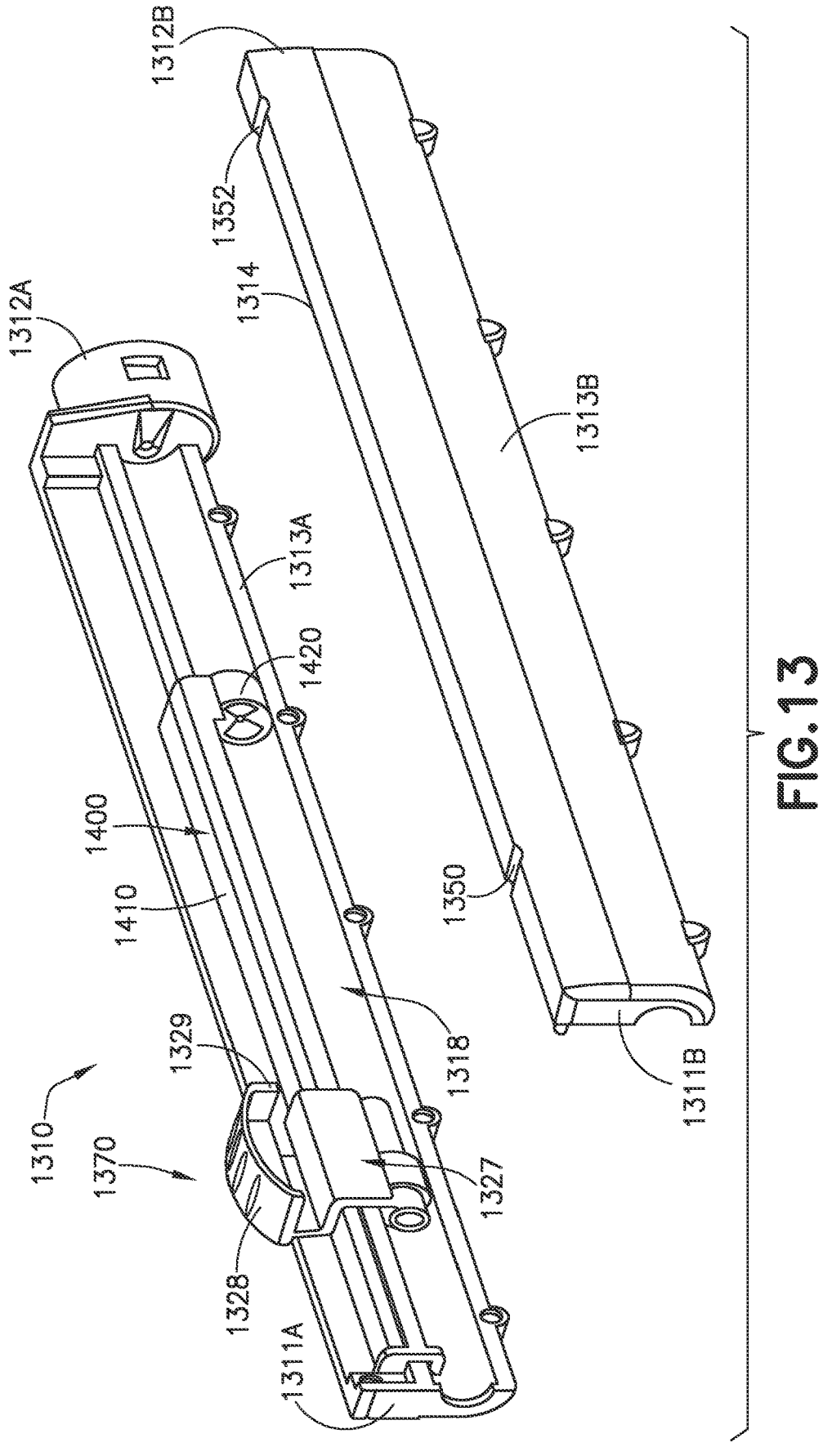
FIG. 13 is an exploded perspective view of an introducer and actuator of a blood draw device in accordance with another aspect of the present disclosure.

Next, referring to FIGS. 12 and 13, introducers and actuators in accordance with alternative aspects of the present disclosure are shown.

First, regarding FIG. 12, an introducer 1100 and actuator 1170 are shown. The introducer 1100 is shown as being constructed in two pieces, with a first body portion 1113A and a second body portion 1113B. The first body portion 1113A includes a proximal end portion 1111A and a distal end portion 1112A, while the second body portion 1113B includes a corresponding proximal end portion 1111B and a distal end portion 1112B. The first body portion 1113A and the second body portion 1113B may be coupled by any appropriate method such as, e.g., one or more fasteners, an adhesive, welding, etc.

An interior portion 1118 of introducer 1100 is formed when the respective body portions 1113A and 1113B are coupled together, with the interior portion 1118 configured to allow for linear displacement of a lower portion 1127 of the actuator 1170 along the introducer 1100. The introducer 1100 also includes a top surface 1114 formed thereon, with a first concave detent 1150 formed in the top surface 1114 near the proximal end portion 1111B of the second body portion 1113B, and a second concave detent 1152 formed in the top surface 1114 near the distal end portion 1112B of the second body portion 1113B.

The actuator 1170 also includes an engagement member 1128, as well as a downwardly-extending tab 1129. The downwardly-extending tab 1129 is configured to selectively engage one or both of the first concave detent 1150 and the second concave detent 1152. However, these detents are not the only restriction or indicator provided on introducer 1100. Instead, a buckle support 1200 is provided, with buckle support 1200 having an exterior portion 1210 and an interior portion 1220. The position of buckle support 1200 along the introducer 1100 defines a location at which the catheter/flow tube (not shown) would be positioned beyond the distal tip of the indwelled catheter within the patient when fed through the introducer 1100 by way of the actuator 1170. That is, as the user slides the actuator 1170 along the introducer 1100, the actuator 1170 eventually contacts the buckle support 1200, signifying to the user that the catheter/flow tube is now beyond the indwelled catheter. Thus, whereas the previous embodiments described herein provided tactile feedback to the user by way of, e.g., a plurality of ridges formed on the introducer, the introducer 1100 as shown in FIG. 12 utilizes the buckle support 1200 to provide this tactile (and visible) feedback to the user.

Referring to FIG. 13, an introducer 1310 and actuator 1370 in accordance with another aspect of the present disclosure are shown. The introducer 1310 is shown as being constructed in two pieces, with a first body portion 1313A and a second body portion 1313B. The first body portion 1313A includes a proximal end portion 1311A and a distal end portion 1312A, while the second body portion 1313B includes a corresponding proximal end portion 1311B and a distal end portion 1312B. The first body portion 1313A and the second body portion 1313B may be coupled by any appropriate method such as, e.g., one or more fasteners, an adhesive, welding, etc.

An interior portion 1318 of introducer 1310 is formed when the respective body portions 1313A and 1313B are coupled together, with the interior portion 1318 configured to allow for linear displacement of a lower portion 1327 of the actuator 1370 along the introducer 1310. The introducer 1310 also includes a top surface 1314 formed thereon, with a first concave detent 1350 formed in the top surface 1314 near the proximal end portion 1311B of the second body portion 1313B, and a second concave detent 1352 formed in the top surface 1314 near the distal end portion 1312B of the second body portion 1313B.

The actuator 1370 also includes an engagement member 1328, as well as a downwardly-extending tab 1329. The downwardly-extending tab 1329 is configured to selectively engage one or both of the first concave detent 1350 and the second concave detent 1352. Furthermore, a buckle support 1400 is provided wholly within the interior portion 1318 of the introducer 1310, with the buckle support 1400 having an elongated portion 1410 and a stopping portion 1420. The position of the stopping portion 1420 of the buckle support 1400 along the introducer 1310 defines a location at which the catheter/flow tube (not shown) would be positioned beyond the distal tip of the indwelled catheter within the patient when fed through the introducer 1310 by way of the actuator 1370. That is, as the user slides the actuator 1370 along the elongated portion 1410 and the introducer 1310, the actuator 1370 eventually contacts the stopping portion 1420 of the buckle support 1400, signifying to the user that the catheter/flow tube is now beyond the indwelled catheter. Thus, whereas the previous embodiments described herein provided tactile feedback to the user by way of, e.g., a plurality of ridges formed on the introducer, the introducer 1310 as shown in FIG. 13 utilizes the buckle support 1400 to provide this tactile feedback to the user.

While various embodiments have been described above, it should be understood that they have been presented by way of example only, and not limitation. Where schematics and/or embodiments described above indicate certain com-ponents arranged in certain orientations or positions, the arrangement of components may be modified. Although various embodiments have been described as having particular features and/or combinations of components, other embodiments are possible having a combination of any features and/or components from any of embodiments as discussed above.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

What is claimed is:

1. A blood draw device for use with a peripheral intravenous catheter (PIVC) comprising:
   an introducer having a proximal end portion, a distal end portion, and an inner volume, the introducer further comprising an exterior top surface and an interior upper surface, the interior upper surface having at least a first portion of a first length and a second portion of a second length, wherein at least one of the first portion and the second portion of the interior upper surface comprises a plurality of ridges formed thereon; and
   an actuator having an exterior portion positioned above the exterior top surface of the introducer and an interior portion positioned within the inner volume of the introducer, wherein the exterior portion of the actuator comprises an engagement member and the interior portion comprises an upwardly-extending tab projecting towards the interior upper surface of the introducer, the actuator configured to move relative to the introducer such that the upwardly-extending tab of the actuator contacts the plurality of ridges formed on at least one of the first portion and the second portion of the interior upper surface of the introducer.

2. The blood draw device of claim 1, wherein both the first portion and the second portion of the interior upper surface comprise a plurality of ridges formed thereon.

3. The blood draw device of claim 2, wherein the plurality of ridges formed on the second portion are larger than the plurality of ridges formed on the first portion.

4. The blood draw device of claim 1, wherein the first portion of the interior upper surface is a smooth surface and the second portion of the interior upper surface comprises the plurality of ridges formed thereon.

5. The blood draw device of claim 1, wherein the second length of the second portion on the interior upper surface is shorter than the first length of the first portion on the interior upper surface.

6. The blood draw device of claim 1, wherein the interior upper surface of the introducer further comprises a convex protrusion located proximate to the proximal end portion of the introducer, and a concave indentation located proximally and adjacent to the convex protrusion.

7. The blood draw device of claim 6, wherein the upwardly-extending tab of the actuator is configured to engage with the concave indentation of the introducer when the actuator is positioned at a proximate-most position relative to the introducer to prevent movement of the actuator without distally-directed force on the engagement member of the actuator.

8. The blood draw device of claim 1, wherein the upwardly-extending tab of the actuator is positioned on a cantilever.

9. The blood draw device of claim 1, wherein the actuator further comprises a spring member configured to provide for releasable engagement of the actuator with a detent formed on the interior upper surface of the introducer.

* * * * *